United States Patent [19]
Ratcliffe et al.

[11] Patent Number: 6,008,212
[45] Date of Patent: Dec. 28, 1999

[54] CARBAPENEM ANTIBACTERIAL COMPOUNDS, COMPOSITIONS CONTAINING SUCH COMPOUNDS AND METHODS OF TREATMENT

[75] Inventors: Ronald W. Ratcliffe, Matawan; Timothy A. Blizzard, Rahway, both of N.J.

[73] Assignee: Merck & Co., Inc., Rahway, N.J.

[21] Appl. No.: 09/168,422

[22] Filed: Oct. 8, 1998

Related U.S. Application Data

[60] Provisional application No. 60/062,121, Oct. 15, 1997.

[51] Int. Cl.$^6$ ....................... A61K 31/395; C07D 487/04
[52] U.S. Cl. ............................................. 514/210; 540/302
[58] Field of Search .............................. 540/302; 514/210

[56] References Cited

U.S. PATENT DOCUMENTS

| | | | |
|---|---|---|---|
| 4,309,438 | 1/1982 | Christensen et al. | 424/274 |
| 4,479,947 | 10/1984 | Christensen | 424/203 |
| 5,756,725 | 5/1998 | Wilkening et al. | 540/302 |

OTHER PUBLICATIONS

Kurt Ritter et al. *Synthesis*, pp. 735–762 (Aug. 1993).

*Primary Examiner*—Mukund J. Shah
*Assistant Examiner*—Ann M. Kessinger

*Attorney, Agent, or Firm*—Sylvia A. Ayler; Mark R. Daniel

[57] ABSTRACT

Compounds of formula I:

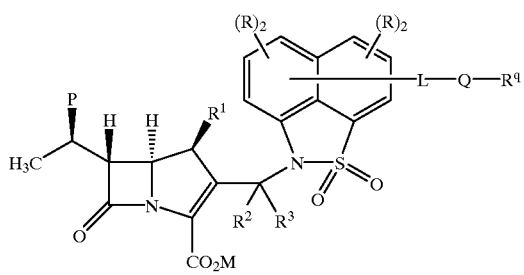

as well as pharmaceutically acceptable salts thereof are disclosed.

$R^2$ is H and $R^3$ is C1–3 alkyl, or $R^2$ and $R^3$ taken in combination represent $C_{1-3}$ alkylidene. Pharmaceutical compositions and methods of treatment are also included. The compounds are useful against methicillin resistant staphylococci (MRSA).

15 Claims, No Drawings

CARBAPENEM ANTIBACTERIAL COMPOUNDS, COMPOSITIONS CONTAINING SUCH COMPOUNDS AND METHODS OF TREATMENT

This application claims benefit of Provisional Application No. 60/062,121 filed Oct. 15, 1997.

BACKGROUND OF THE INVENTION

The present invention relates to carbapenem antibacterial agents in which the carbapenem nucleus is substituted at the 2-position with a naphthosultam linked through a $CR^2R^3$ group. The naphthosultam is further substituted with various substituent groups including at least one cationic group —L—Q—$R^q$.

The carbapenems of the present invention are usefull against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy for treating infections caused by these difficult to control pathogens.

There is an increasing need for agents effective against such pathogens (MRSA/MRCNS) which are at the same time relatively free from undesirable side effects.

SUMMARY OF THE INVENTION

The compounds of the invention are represented by formula I:

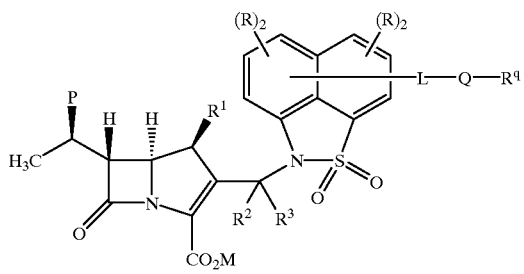

including pharmaceutically acceptable salts thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

$R^2$ is H and $R^3$ is C1–3 alkyl, or $R^2$ and $R^3$ taken in combination represent $C_{1-3}$ alkylidene;

L is $C_{1-4}$ straight or branched alkylene, uninterrupted, interrupted or terminated by 1–2 of O, S, $NR^a$, C(O), $CO_2$ and $C(O)NR^a$;

Q represents:

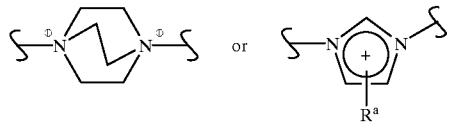

$Y^-$ is a charge balancing group;

$R^a$ is H or C1–6 alkyl;

$R^q$ is $C_{1-6}$ alkyl, straight or branched, uninterrupted, interrupted or terminated by 1–2 of O, S, $NR^a$, C(O), C(O)O, $C(O)NR^a$, —CH=CH—, -Het($R^b$)$_3$—, —C(O)Het($R^b$)$_3$—, —C(O)$NR^a$Het($R^b$)$_3$—

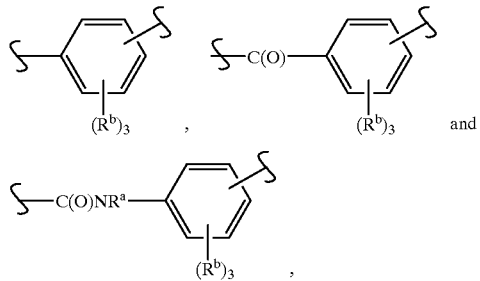

said $R^q$ being unsubstituted or substituted with 1–3 $R^c$ groups;

Het is a heteroaryl group;

each $R^b$ is independently selected from H, halo, $OR^a$, $OC(O)R^a$, $C(O)R^a$, CN, $C(O)NR^aR^d$, $NO_2$, $NR^aR^d$, $SO_2NR^aR^d$ and $C_{1-4}$ alkyl unsubstituted or substituted with 1–3 groups selected from $R^e$;

each $R^c$ is independently selected from halo, $C_{1-4}$ alkyl, $OR^f$, $OC(O)R^f$, $SR^f$, $S(O)R^f$, $SO_2R^f$, CN, $C(O)R^f$, $CO_2R^f$, $NR^fRg$, $C(O)NR^aR^f$, -Het($R^b$)$_3$, $C(=N^+R^aR^f)R^a$, $C(=N^+R^aR^f)NR^aR^f$, $NR^aC(=N^+R^aR^f)R^a$, $NR^aC(=N^+R^aR^f)NR^aR^f$, heteroarylium($R^b$)$_3$, $SO_2NR^aR^f$, $OC(O)NR^aR^f$, $NR^aC(O)R^f$, $NR^aC(O)NR^aR^f$, and

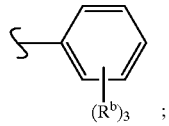

or in the alternative, when 2 or more $R^c$ groups are present, 2 $R^c$ groups may be taken together with any intervening atoms to form a 3–6 membered carbocyclic ring, optionally interrupted with 1–3 of O, S, $NR^g$, and C(O), said ring being unsubstituted or substituted with 1–3 $R^e$ groups,;

$R^d$ is H or $C_{1-4}$ alkyl, or $R^a$ and $R^d$ taken together with any intervening atoms represent a 4–6 membered ring;

each $R^e$ is independently selected from halo, $OR^a$, $NR^aR^d$ and $CONR^aR^d$;

$R^f$ is H; $C_{1-6}$ straight or branched chain alkyl, unsubstituted or substituted with 1–3 $R^e$ groups; -Het($R^b$)$_3$; $C_{3-6}$ cycloalkyl, unsubstituted or substituted with 1–3 $R^e$ groups, and

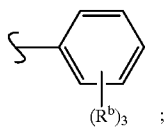

or $R^a$ and $R^f$ together with an intervening atoms form a 4–6 membered ring, optionally interrupted by O, S, $NR^a$ or C(O);

Rg is H, $C_{1-6}$ alkyl, unsubstituted or substituted with 1–3 $R^e$ groups; $C_{3-6}$ cycloalkyl, unsubstituted or substituted with 1–3 $R^e$ groups; $C(=NR^aR^f)R^a$ or $C(=NR^aR^f)NR^aR^f$, or $R^f$ and $R^g$ together with any intervening atoms form a 4–6 membered ring optionally interrupted by O, S, $NR^a$ or C(O);

and each R independently represents $R^b$,

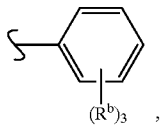

-Het($R^b$)3 or $C_{2-6}$ alkenyl, or one R group may be taken with L and any intervening atoms to represent a 5–6 membered ring.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 15 carbon atoms unless otherwise defined. It may be straight or branched. Preferred alkyl groups include methyl, ethyl, propyl, isopropyl, butyl and t-butyl. When substituted, alkyl groups may be substituted with up to 3 substituent groups, selected from $R^b$, $R^c$, $R^e$ and $R^q$ as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused. Preferred cycloalkyl groups are cyclopropyl, cyclobutyl, cyclopentyl and cyclohexyl. When substituted, cycloalkyl groups may be substituted with up to 3 substituents selected from $R^c$, $R^c$, $R^q$ and $R^e$.

A C1–4 alkylene group refers to an alkyl group which is attached through two bonds to two different atoms or substituents. The two bonds on the alkylene group can be on the same carbon atom or on different carbon atoms. See, e.g., the following:

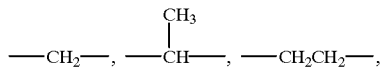

-continued

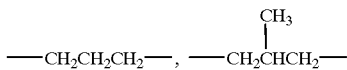

A $C_{1-3}$ alkylidene refers to an alkyl group which is attached through two bonds on the same carbon atom of the alkyl group to a single attachment atom. See, e.g. the following:

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms. The preferred aryl groups are phenyl, naphthyl and phenanthrenyl. Aryl groups may likewise be substituted as defined. Preferred substituted aryls include phenyl and naphthyl.

The term "heteroaryl" (Het) refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, and thiazole. Additional nitrogen atoms may be present together with the first nitrogen and oxygen or sulfur, giving, e.g., thiadiazole. Examples include the following:

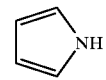  

pyrrole (pyrrolyl)  imidazole (imidazolyl)  thiazole (thiazolyl)

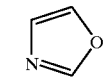  

oxazole (oxazolyl)  furan (furyl)  thiophene (thienyl)

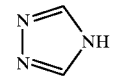  

triazole (triazolyl)  pyrazole (pyrazolyl)  isoxazole (isoxazolyl)

  

isothiazole (isothiazolyl)  pyridine (pyridinyl)  pyrazine (pyrazinyl)

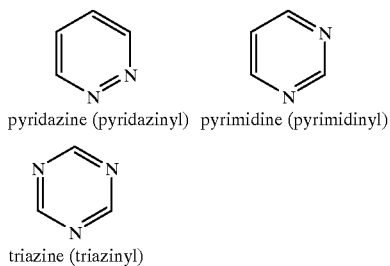

pyridazine (pyridazinyl)   pyrimidine (pyrimidinyl)

triazine (triazinyl)

The group L—Q—R$^q$ is attached to either of the two phenyl rings of the naphthosultam group, provided that no more than one L—Q—R$^q$ group is present.

Heteroarylium refers to heteroaryl groups bearing a quaternary nitrogen atom and thus a positive charge. Examples include the following:

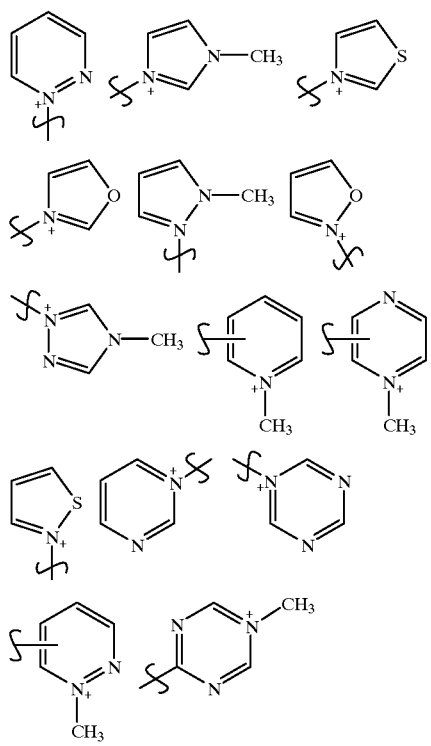

When a charge is shown on a particular nitrogen atom in a ring which contains one or more additional nitrogen atoms, it is understood that the charge may reside on a different nitrogen atom in the ring by virtue of charge resonance that occurs.

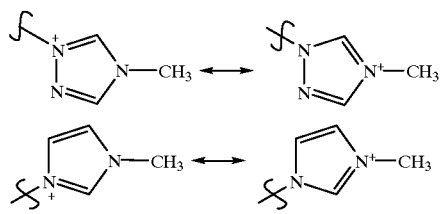

The imidazolium group:

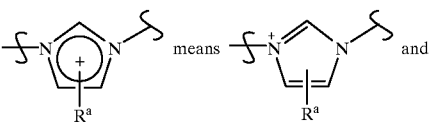

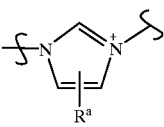

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methylpyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

When a group is termed "substituted", unless otherwise indicated, this means that the group contains from 1 to 4 substituents thereon.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis Wiley*, New York (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable C-6 hydroxyethyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Acid addition salts of the compounds of formula I include compounds that contain a protonated, basic moiety in $R^q$ or R. Compounds containing a basic moiety in $R^q$ or R are capable of protonation in aqueous media near pH 7, so that the basic moiety can exist as an equilibrium mixture of its neutral form and acid addition (protonated) form. The more basic the group, the greater the degree of protonation near pH 7. For example, —$NR^fR^g$ would likely be present in its protonated form, —$N^+HR^fR^g$ $X^-$ at the appropriate pH, where $X^-$ is a charge balancing group. All such compounds are included in the present invention.

For the purposes of this invention, all compounds which have one or more cations are balanced with one or more, as necessary, of a charge balancing group $X^-$ or $Y^-$. Examples of cases where a charge balancing group is required are quarternized substituents such as heteroarylium or C(=$N^+$ $R^aR^f)R^a$, where $R^a$ and $R^f$ are not H. Additionally, all compounds having one or more anions are counter balanced with one or more, as necessary, charge balancing counterion.

When a group is interrupted by 2–3 of O, S, or N they cannot form O—O, O—O—O, O—S, O—S—O, S—S, or S—S—S bonds. This is exemplified in the case when L or Rq is an alkyl interrupted or terminated by 1–2 of O, S, $NR^a$, C(O), $CO_2$ or $C(O)NR^a$.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$X^-$ and $Y^-$ can be present or absent as necessary to maintain the appropriate charge balance. When present, these represent pharmaceutically acceptable counterions. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when more than one negative charge is necessary to maintain charge neutrality, the counterion indicator may represent a specie with more than one negative charge, such as malonate, tartrate or ethylenediaminetetraacetate (EDTA), or two or more monovalent anions, such as chloride, etc. When a multivalent negatively charged counterion is present with a carbapenem which bears a net single positive charge, an appropriate number of carbapenem molecules can be found in association therewith to maintain the overall charge balance and neutrality.

Numbering and nomenclature using in naming the naphthosultams are as follows:

Naphthosultam Nomenclature
Chemical Abstracts

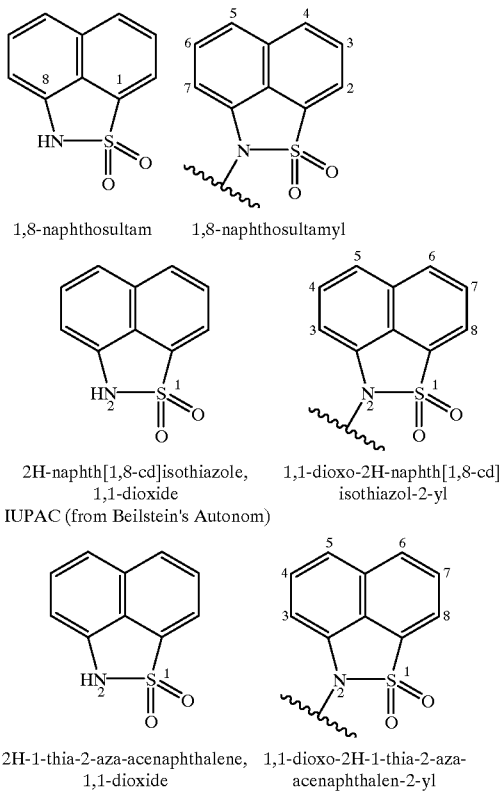

1,8-naphthosultam     1,8-naphthosultamyl 2H-naphth[1,8-cd]isothiazole,    1,1-dioxo-2H-naphth[1,8-cd]
1,1-dioxide                      isothiazol-2-yl IUPAC (from Beilstein's Autonom)

2H-1-thia-2-aza-acenaphthalene,    1,1-dioxo-2H-1-thia-2-aza-
1,1-dioxide                      acenaphthalen-2-yl When L is a $C_{1-4}$ straight or branched alkylene group that is interrupted or terminated by 1–2 of O, S, $NR^a$, C(O), $CO_2$ and $C(O)NR^a$, the interrupting/terminating moiety or moieties can be at either end of the alkylene group, as well as interrupting the alkylene group when 2–4 carbon atoms are present. When 2 such groups are present, they may be separate or together. Hence, interrupting or terminating groups such as OC(O) and $OCO_2$ are included.

Similarly, when Rq is $C_{1-6}$ alkyl, straight or branched, interrupted or terminated by 1–2 of O, S, $NR^a$, C(O), C(O)O, $C(O)NR^a$, —CH=CH—, -Het$(R^b)_3$—. —C(O)Het$(R^b)_3$—, —C(O)$NR^a$Het$(R^b)_3$—,

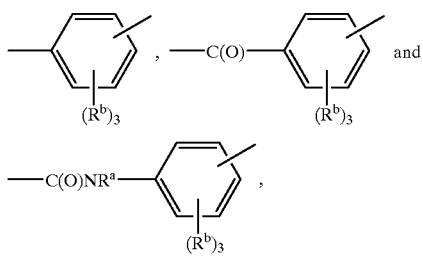

said $R^q$ being unsubstituted or substituted with 1–3 $R^c$ groups; the interrupting groups may be separate or together, and may be at the end or ends of the alkyl group, and further may be between the alkyl group and a substituent $R^c$, the terminating groups may be separate or together, and may be between the Q and $R^q$, and further may be between the alkyl group and a substituent $R^c$.

When an $R^q$ is substituted with at least 2 $R^c$ groups, these may be taken in combination with any intervening atoms to represent a 3–6 membered carbocyclic ring, said ring being optionally interrupted by 1–3 of O, S, $NR^g$ and C(O), and unsubstituted or substituted with 1–3 $R^e$ groups. Examples of groups which are represented by two $R^c$ groups in combination include the following:

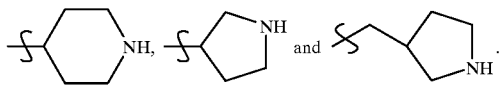

Regarding substitution with $R^2$ and $R^3$, such as when $R^2$ represents H and the $R^3$ represents $C_{1-3}$ alkyl, the compounds may exist in R and S stereoisomeric forms at the $CR^2R^3$ stereocenter. Both isomers are included in the present invention, in pure form as well as in mixture.

When $R^2$ and $R^3$ taken in combination represent $C_{2-3}$ alkylidene, both E and Z isomers across the double bond are included, in pure form as well as in mixture. Representative examples are as follows:

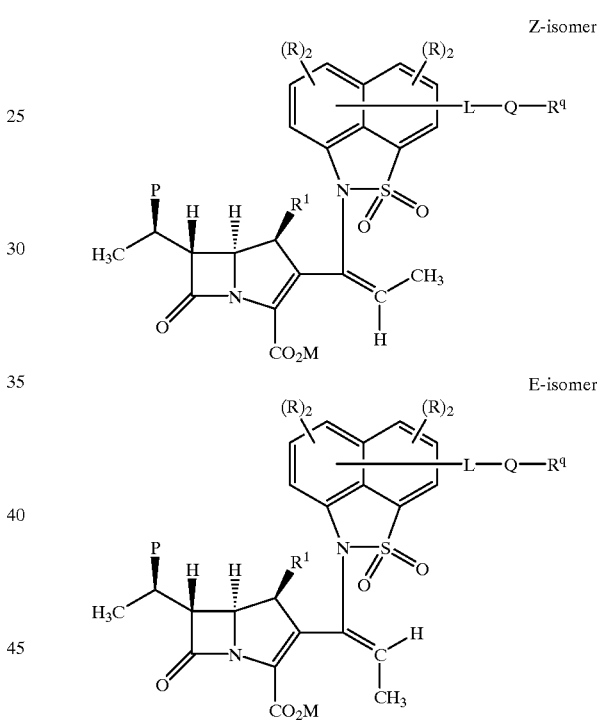

A subset of compounds of formula I which is of interest relates to those compounds where $R^1$ represents methyl. Within this subset, all other variables are as originally defined.

Another subset of compounds of formula I which is of interest relates to those compounds where $CO_2M$ represents a carboxylate anion. Hence, M in this instance represents a negative charge which is balanced by a positively charged group, such as in the positively charged Q group. Likewise, if the positively charged Q group contains more than one positive charge, a negatively charged counterion may be present which in combination with the carboxylate anion, provides overall charge neutrality.

Another subset of compounds of formula I that is of interest relates to those compounds where P represents hydroxyl or hydroxyl protected by a hydroxyl protecting group. Within this subset, all other variables are as originally defined.

Another subset of compounds of formula I that is of interest relates to those compounds where $R^2$ represents H and $R^3$ is $C_{1-3}$ alkyl. In particular, $R^2$ represents H and $R^3$ represents $CH_3$ (Me) or ethyl (Et). Within this subset, all other variables are as originally defined.

Another subset of compounds of formula I that is of interest relates to those compounds where $R^2$ and $R^3$ are taken in combination, and represent $C_{1-3}$ alkylidene. Preferably $R^2$ and $R^3$ are taken in combination to represent $=CH_2$ or $=CHMe$. Within this subset, all other variables are as originally defined.

Another subset of compounds of formula I that is of interest relates to compounds where L represents $—CH_2—$ or $—CH_2CH_2—$. Within this subset, all other variables are as originally defined.

Another subset of compounds of formula I that is of interest relates to compounds where Q represents wherein $Y^-$ represents a charge balancing group. Within this subset, all other variables are as originally defined.

Another subset of compounds of formula I that is of interest relates to compounds where $R^q$ is straight or branched $C_{1-6}$ alkyl, substituted with 1–3 $R^c$ groups. Within this subset, all other variables are as originally defined.

Another subset of compounds of formula I that is of interest relates to compounds where R is H, halo or $C_{1-4}$ alkyl unsubstituted or substituted with 1–3 groups selected from $R^e$ Within this subset, all other variables are as originally defined.

A preferred subset of compounds of formula I which is of interest relates to those compounds wherein:

$R^1$ represents $CH_3$;

$CO_2M$ represents a carboxylate anion;

P represents hydroxyl or hydroxyl protected by a hydroxyl protecting group;

each R is independently H, halo or $C_{1-4}$ alkyl unsubstituted or substituted with 1–3 groups selected from $R^e$;

$R^a$ is H or C1–6 alkyl;

$R^d$ is H or $C_{1-4}$ alkyl, or $R^a$ and $R^d$ taken together with any intervening atoms represent a 4–6 membered ring;

$R^e$ is halo, $OR^a$, $NR^aR^d$ or $CONR^aR^d$;

$R^2$ represents H and $R^3$ is $C_{1-3}$ alkyl;

L represents $—CH_2—$ or $—CH_2CH_2—$;

Q represents wherein $Y^-$ represents a charge balancing group and $R^q$ is straight or branched $C_{1-6}$ alkyl, optionally interrupted by $C(O)NR^a$ or and substituted with 1–3 $R^c$ groups, and $R^c$ is as originally defined.

More preferably, $R^2$ is H and $R^3$ is $CH_3$ or $CH_2CH_3$.

Another preferred subset of compounds of formula relates to those compounds of formula I wherein:

$R^1$ represents methyl;

$CO_2M$ represents a carboxylate anion;

P represents hydroxyl or hydroxyl protected by a hydroxyl protecting group;

R is H, halo or $C_{1-4}$ alkyl unsubstituted or substituted with 1–3 groups selected from $R^e$;

$R^a$ is H or $C_{1-6}$ alkyl;

$R^d$ is H or $C_{1-4}$ alkyl, or $R^a$ and $R^d$ taken together with any intervening atoms represent a 4–6 membered ring;

$R^e$ is halo, $OR^a$, $NR^aR^d$ or $CONR^aR^d$;

$R^2$ and $R^3$ are taken in combination, and represent $C_{1-3}$ alkylidene;

L represents $—CH_2—$ or $—CH_2CH_2—$;

Q represents wherein $Y^-$ represents a charge balancing group and

Rq is straight or branched C1–6 alkyl, substituted with 1–3 $R^c$ groups.

More particularly, $R^2$ and $R^3$ are taken in combination to represent $=CH_2$ or $=CHMe$.

Representative examples of compounds of the invention are found in Table I.

TABLE I n = 1 or 2,    R = H, Cl, Br

| | 3' or 4' L—Q—Rq | $R^2 + R^3 =$ |
|---|---|---|
| 1 |  —(CH$_2$)$_n$—N⊕=\\N—CH$_3$ | H, Me |

TABLE I-continued n = 1 or 2, R = H, Cl, Br

| | 3' or 4' L—Q—Rq | $R^2 + R^3 =$ |
|---|---|---|
| 2 | —(CH$_2$)$_n$—imidazolium—N—CH$_3$ | H, Et |
| 3 | —(CH$_2$)$_n$—imidazolium—N—CH$_3$ | =CH$_2$ |
| 4 | —(CH$_2$)$_n$—imidazolium—N—CH$_3$ | =CHCH$_3$ |
| 5 | —(CH$_2$)$_n$—imidazolium—N—CH$_2$CH$_2$OH | H, Me |
| 6 | —(CH$_2$)$_n$—imidazolium—N—CH$_2$CH$_2$OH | H, Et |
| 7 | —(CH$_2$)$_n$—imidazolium—N—CH$_2$CH$_2$OH | =CH$_2$ |
| 8 | —(CH$_2$)$_n$—imidazolium—N—CH$_2$CH$_2$OH | =CHCH$_3$ |
| 9 | —(CH$_2$)$_n$—N⊕(DABCO)N⊕—CH$_2$C(O)NH$_2$  Cl⁻ | H, Me |
| 10 | —(CH$_2$)$_n$—N⊕(DABCO)N⊕—CH$_2$C(O)NH$_2$  Cl⁻ | H, Et |
| 11 | —(CH$_2$)$_n$—N⊕(DABCO)N⊕—CH$_2$C(O)NH$_2$  Cl⁻ | =CH$_2$ |
| 12 | —(CH$_2$)$_n$—N⊕(DABCO)N⊕—CH$_2$C(O)NH$_2$  Cl⁻ | =CHCH$_3$ |
| 13 | —(CH$_2$)$_n$—N⊕(DABCO)N⊕—(CH$_2$)$_3$OH  Cl⁻ | H, Me |
| 14 | —(CH$_2$)$_n$—N⊕(DABCO)N⊕—(CH$_2$)$_3$OH  Cl⁻ | H, Et |
| 15 | —(CH$_2$)$_n$—N⊕(DABCO)N⊕—(CH$_2$)$_3$OH  Cl⁻ | =CH$_2$ |
| 16 | —(CH$_2$)$_n$—N⊕(DABCO)N⊕—(CH$_2$)$_3$OH  Cl⁻ | =CHCH$_3$ |
| 17 | —(CH$_2$)$_n$—N⊕(DABCO)N⊕—(CH$_2$)$_3$NH$_3$⊕  2 Cl⁻ | H, Me |
| 18 | —(CH$_2$)$_n$—N⊕(DABCO)N⊕—(CH$_2$)$_3$NH$_3$⊕  2 Cl⁻ | H, Et |
| 19 | —(CH$_2$)$_n$—N⊕(DABCO)N⊕—(CH$_2$)$_3$NH$_3$⊕  2 Cl⁻ | =CH$_2$ |
| 20 | —(CH$_2$)$_n$—N⊕(DABCO)N⊕—(CH$_2$)$_3$NH$_3$⊕  2 Cl⁻ | =CHCH$_3$ |

TABLE I-continued

Structure I: n = 1 or 2, R = H, Cl, Br

| # | 3' or 4' L—Q—Rq | R² + R³ = |
|---|---|---|
| 21 | —(CH₂)ₙ—N⁺(DABCO)N⁺—CH₂C(O)NH—CH₂CH₂—NH₃⁺  2 Cl⁻ | H, Me |
| 22 | —(CH₂)ₙ—N⁺(DABCO)N⁺—CH₂C(O)NH—CH₂CH₂—NH₃⁺  2 Cl⁻ | H, Et |
| 23 | —(CH₂)ₙ—N⁺(DABCO)N⁺—CH₂C(O)NH—CH₂CH₂—NH₃⁺  2 Cl⁻ | =CH₂ |
| 24 | —(CH₂)ₙ—N⁺(DABCO)N⁺—CH₂C(O)NH—CH₂CH₂—NH₃⁺  2 Cl⁻ | =CHCH₃ |
| 25 | —(CH₂)ₙ—N⁺(DABCO)N⁺—CH₂C(O)—C₆H₄—CH₂CH₂—NH₃⁺  2 Cl⁻ | H, Me |
| 26 | —(CH₂)ₙ—N⁺(DABCO)N⁺—CH₂C(O)—C₆H₄—CH₂CH₂—NH₃⁺  2 Cl⁻ | H, Et |
| 27 | —(CH₂)ₙ—N⁺(DABCO)N⁺—CH₂C(O)—C₆H₄—CH₂CH₂—NH₃⁺  2 Cl⁻ | =CH₂ |
| 28 | —(CH₂)ₙ—N⁺(DABCO)N⁺—CH₂C(O)—C₆H₄—CH₂CH₂—NH₃⁺  2 Cl⁻ | =CHCH₃ |

The compounds of the present invention are synthesized using the general conditions shown in the accompanying flow charts.

Flow Chart I

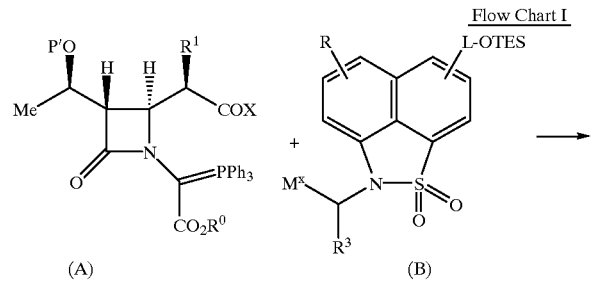

(A) + (B) →

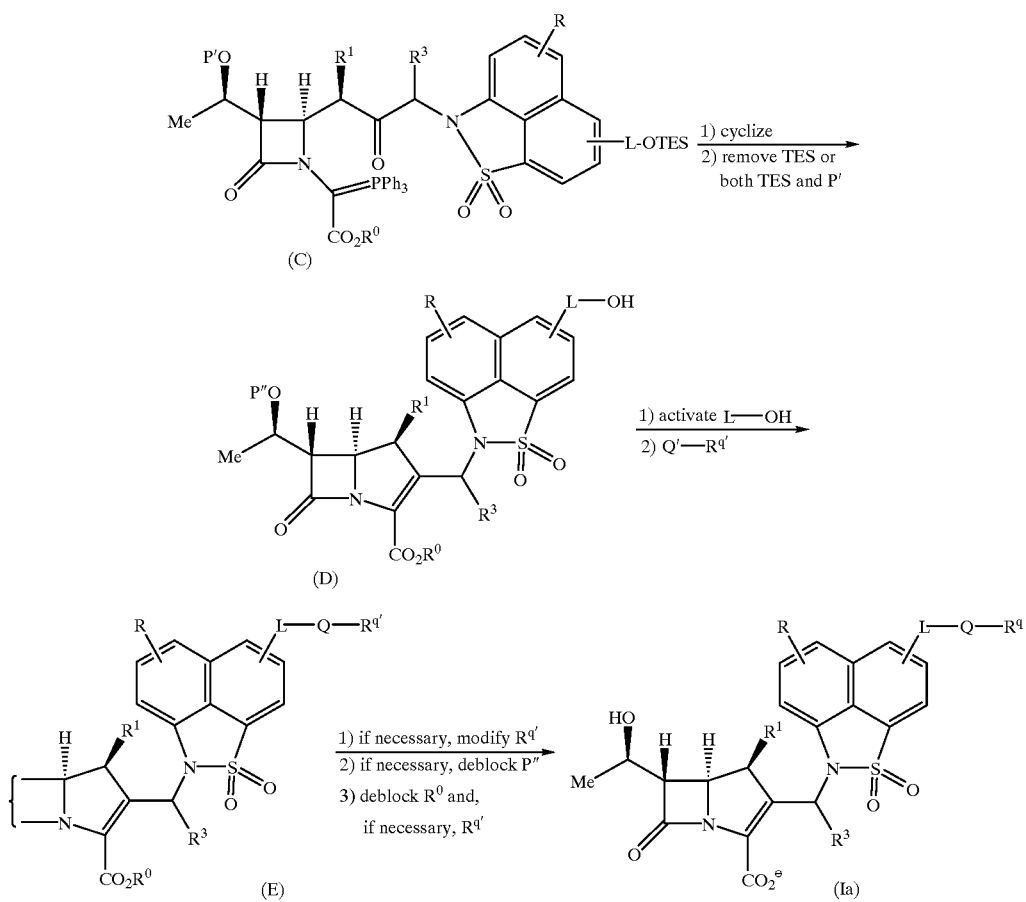
P' = TBS or TES, P'' = H, TES or TBS
X = S-Pyr or N(Me)OMe
$M^x$ = Li, ClMg or BrMg
$R^0$ = allyl, PMB or PNB
Q' = neutral or monocationic precursor to Q
$R^{q'}$ = $R^q$ or a modified/protected precursor to $R^q$
Flow Chart II
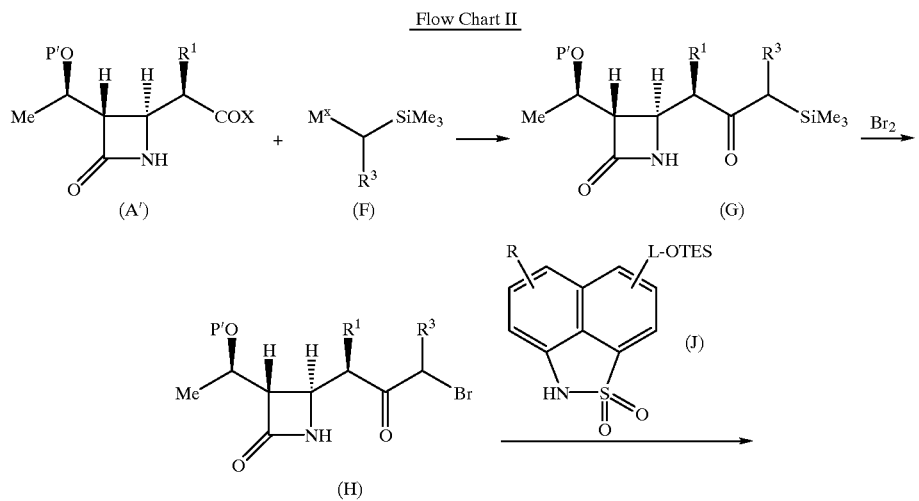

-continued
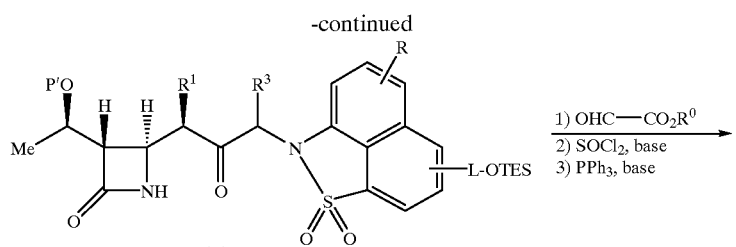
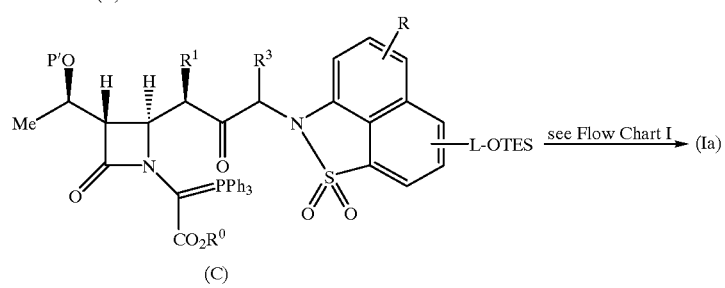
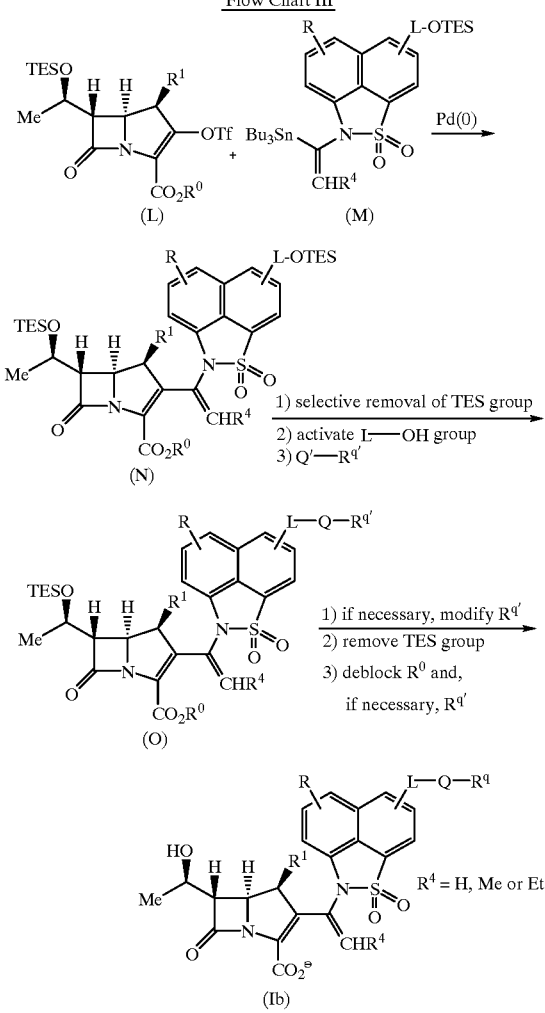

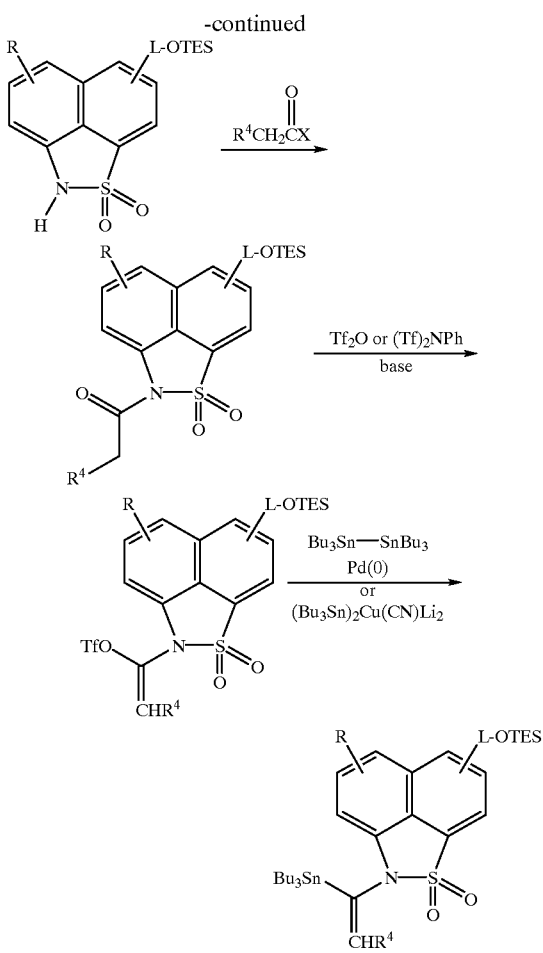

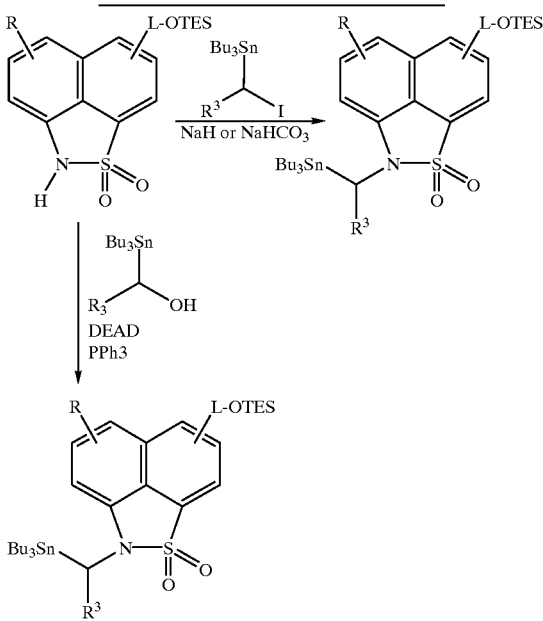

Flow Chart V
Preparation of Naphthosultam Intermediates

Compounds of formula I wherein $R^2$ is H and $R^3$ is $C_{1-3}$ alkyl can be synthesized by combining a metallated naph-thosultam (B) with an ylide substituted monocyclic B-lactam (A) containing an activated carboxylic acid derivative. This is shown in Flow Chart I. The resulting ketone (C) is cyclized by heating in an inert solvent to produce, after removal of the triethylsilyl (TES) protecting group, the naphthosultamyl-methyl substituted carbapenem (D). The reaction of (A) and (B) is conducted in an inert organic solvent such as THF, under a nitrogen or argon atmosphere, at reduced temperature. The metallated species (B) is prepared from the corresponding tributylstannane substituted naphthosultam (See Flow Chart V) by low temperature treatment with BuLi or BuLi/MgX'$_2$ (X'=halide).

The TES protected hydroxyl group in (C) or, preferably, its cyclized carbapenem product, can be deprotected using an acid, such as triflic acid, or a fluoride source, such as Bu$_4$NF. The alcohol group of (D) can be activated towards replacement by the nucleophile Q'—R$^{q'}$, in any of a number of ways. For example, when L is CH$_2$, the hydroxyl group can be converted to a sulfonate derivative, such as methanesulfonyloxy, and then to an iodide derivative. When L is CH$_2$CH$_2$, the hydroxy group can be converted to a trifluoromethanesulfonyloxy (triflate) derivative by reaction with triflic anhydride. The activated intermediate can be combined with the reagent Q'—R$^{q'}$ in an inert solvent or neat to provide the displacement product (E). This may involve a neutral moiety which becomes mono-quaternary upon reaction or a mono-quaternary moiety which becomes bis-quaternary upon reaction.

Modification of the substituent Rq', if necessary, and removal of the remaining protecting group(s) affords the final product (Ia). These transformations can be accomplished by a number of well known techniques depending on the protecting groups employed or the modifications required to transform Rq' to Rq. For example, when $R^o$ is allyl, deprotection is accomplished uising a Pd(0) catalyzed allyl transfer whereas when $R^o$ is p-nitrobenzyl, deprotection is accomplished by catalytic hydrogenation.

Alternatively, as shown in Flow Sheet II, monocylic B-lactam (A') which contains an activated carboxylic acid derivative can be reacted with a metallated trimethylsilyla-lkane (F) to afford the silylalkyl ketone (G). Intermediates of type (F) are well known and easily prepared. Bromination of (G) affords the bromoalkyl ketone (H) which can be reacted with a naphthosultam (J) in the presence of a base, such as NaHCO$_3$ or NaH, to afford the intermediate (K). The azetidinone (K) can be converted to the ylide (C) using the standard, three-step process involving sequential reactions with a glyoxylic acid ester, a chlorinating agent such as SOCl$_2$, and triphenylphosphine. The B-lactam ylide (C) can be processed as described above (See Flow Chart I) to afford final products Ia.

Compounds of formula I wherein $R^2$ and $R^3$ taken in combination represents a $C_{1-3}$ alkylidene group can be prepared according to the scheme outlined in Flow Chart III. The naphthosultam substituted carbapenem (N) is prepared using a Pd(0) catalyzed coupling of the carbapenem triflate (L) and the vinyl stannane (M). The coupling reaction can be performed under a variety of conditions which have been well documented in the literature (see, e.g., Ritter, K. *Synthesis* (1993), 735–762). Selective removal of the triethylsilyl protecting group on the naphthosultam side chain of intermediate (N) can be accomplished using a fluoride reagent such as Bu$_4$NF. The rsulting alcohol can be activated and displaced with Q'—Rq' to give intermediate (O). These transformations and the conversion of (O) to final product (Ib) are analogous to the reactions discussed above in connection with Flow Chart I.

The naphthosultamyl vinyl stannane (M) which is used in the cross coupling reaction to produce the carbapenem intermediate (N) can be prepared by the methods described in Flow Chart IV. The naphthosultam precursor to the organometallic species (B) employed in Flow Chart I can be prepared by the methods outlined in Flow Chart V. The reactions shown in Flow Charts IV and V are analogous to reactions previously described for the N-functionalization of carbamate and imide substrates.

The invention is further described in connection with the following non-limiting examples.

PREPARATIVE EXAMPLE 1

Synthesis of 4-(2-triethylsilanyloxy-ethyl)-1,8-naphthosultam

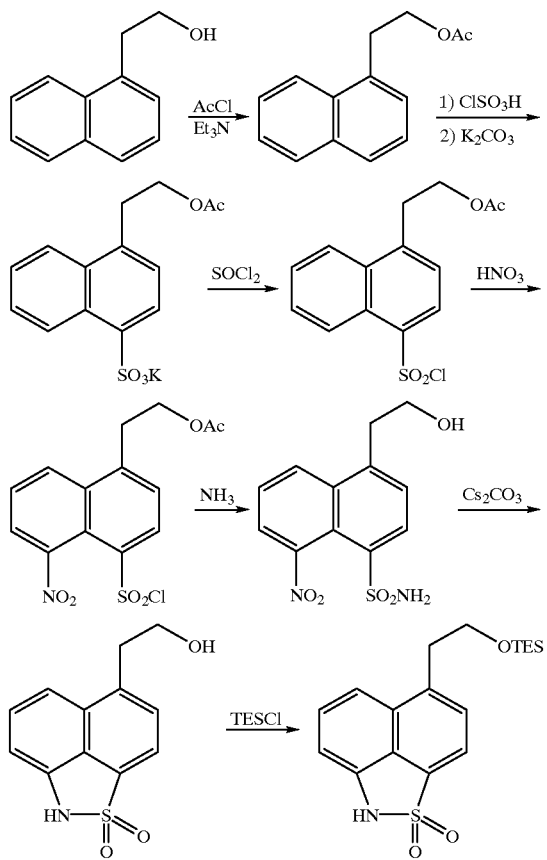

Step 1
1-(2-Acetoxy-ethyl)-naphthalene

Triethylamine (691 mL, 4.96 mol) was added to an ice cold solution of 1-(2-hydroxy-ethyl)-naphthalene (569 g, 3.30 mol) in dichloromethane (2.2 L). Acetyl chloride (282 mL, 3.97 mol) was added dropwise over 90 minutes. After the addition was complete, the reaction mixture was stirred for an additional 30 minutes with ice-bath cooling. The reaction mixture was washed sequentially with water (2×1 L), 1N HCl (1 L, 500 mL), water (1 L), 5% aqueous NaHCO$_3$ (500 mL), water (1 L), and brine (500 mL), then dried over magnesium sulfate, filtered, and evaporated to afford 1-(2-acetoxy-ethyl)-naphthalene (723.2 g) as a yellow oil that slowly crystallized.

Step 2
Potassium 4-(2-acetoxy-ethyl)-naphthalene-1-sulfonate

Chlorosulfonic acid (69.3 g, 590 mmol) was added dropwise over 17 minutes to a solution of 1-(2-acetoxy-ethyl)-naphthalene (105.5 g, 490 mmol) in dichloromethane (200 mL). The reaction was exothermic and periodic ice-bath cooling was employed to maintain the internal temperature at 25–30° C. Approximately 10 minutes into the ClSO$_3$H addition, voluminous evolution of HCl gas was observed. After the addition was complete, the reaction mixture was stirred at room temperature for 3 hours then cautiously added to ice (400 g). After shaking, the layers were separated. The aqueous layer was washed with dichloromethane then slowly neutralized by addition of a solution of potassium carbonate (77 g, 560 mmol) in water (200 mL). The precipitate was collected by filtration, washed with cold water (100 mL), then dried under vacuum at 60° C. to afford potassium 4-(2-acetoxy-ethyl) naphthalene sulfonate (102.39 g) as a white solid. This material contained ca. 6% of the isomeric potassium 5-(2-acetoxy-ethyl)-1-naphthalene sulfonate as determined by 1H NMR. The filtrate was concentrated under vacuum to afford a white suspension (355 g) which was stored in a refrigerator overnight. The solid was collected by filtration, washed with cold water (100 mL), then dried under vacuum at 60° C. to afford a second crop of potassium 4-(2-acetoxy-ethyl) naphthalene-1-sulfonate (10.67 g) as a white solid. The second crop contained ca. 14% of the isomeric potassium 5-(2-acetoxy-ethyl)-1-naphthalene sulfonate as determined by 1H NMR.

Step 3
4-(2-Acetoxy-ethyl)-naphthalene-1-sulfonyl chloride

Potassium 4-(2-acetoxy-ethyl)-naphthalene-1-sulfonate (102.3 g, 308 mmol) was added in portions over 15 minutes to a room temperature solution of dimethylformamide (2.4 mL, 31 mmol) in thionyl chloride (112 mL, 1.54 mol). The reaction mixture was gradually brought to 80° C. (oil bath temperature) over 30 minutes and heated at 80° C. for 90 minutes, then cooled to room temperature and stirred at room temperature for 60 minutes. The reaction mixture was partitioned between ice water (500 mL) and ethyl acetate (500 mL). The organic layer was washed with water (200 mL) and brine (200 mL), dried over magnesium sulfate, filtered, and evaporated under vacuum to a cream colored solid. The crude product was triturated with pet ether to afford 4-(2-acetoxy-ethyl)-naphthalene-1-sulfonyl chloride as a pale tan solid (77.47 g).

Step 4
4-(2-Acetoxy-ethyl)-8-nitro-naphthalene-1-sulfonyl chloride 4-(2-Acetoxy-ethyl)-naphthalene-1-sulfonyl chloride (76.96 g, 246 mmol) was added portionwise over 12 minutes to 90% nitric acid (154 mL, 3.278 mol) cooled in an ice-methanol bath (−20° C.). After the addition was complete, the reaction mixture was stirred at −20° C. for an additional 15 minutes. The reaction mixture was partitioned between ice water (800 mL) and chloroform (800 mL). The aqueous layer was extracted with chloroform (100 mL). The combined organic layers were washed with brine (400 mL, 200 mL), then dried over magnesium sulfate, filtered, and evaporated to a golden oil. Diethyl ether (300 mL) was added to the crude product and the mixture was shaken vigorously to afford an off-white solid. The solid was collected by filtration, washed with ether (2×50 mL), and dried under vacuum to afford 4-(2-acetoxyethyl)-8-nitro-naphthalene-1-sulfonyl chloride (41.85 g) as an off-white solid.

Step 5
4-(2-Hydroxy-ethyl)-8-nitro-naphthalene-1-sulfonamide

Solid 4-(2-acetoxy-ethyl)-8-nitro-naphthalene-1-sulfonyl chloride (39.64 g, 111 mmol) was added to an ice-cold, 6.8

M solution of ammonia in methanol (408 mL, 277 mmol). The cooling bath was removed, the reaction flask was stoppered, and the reaction was stirred at room temperature. After 4 days, the dark amber solution was concentrated under vacuum to a dark gum. The residue was triturated vigorously shaken with water (300 mL) to give a solid which was washed with water (150 mL) then ether (150 mL) and dried under vacuum. The resulting brown solid was recrystallized from isopropanol (300 mL) to afford 4-(2-hydroxy-ethyl)-8-nitro-naphthalene-1-sulfonamide (27.79 g) as tan flakes.

Step 6

4-(2-Hydroxy-ethyl)-1 8-naphthosultam

Powdered cesium carbonate (76.8 g, 236 mmol) was added to a solution of 4-(2-hydroxy-ethyl)-8-nitro-naphthalene-1-sulfonamide (30.77 g, 94.3 mmol) in anhydrous dimethylformamide (470 mL). The mixture was placed under a nitrogen atmosphere, sonicated for 10 minutes, then stirred at room temperature for 20 minutes. The mixture was then placed in a 100° C. oil bath and stirred vigorously. After 3.5 hours, the reaction mixture was removed from the heating bath, allowed to cool to room temperature, and left at room temperature overnight. The mixture was then filtered and the collected solid was washed with dimethylformamide. The combined filtrate and washings were evaporated to a dark oil. This material was dissolved in water (400 mL), treated with activated charcoal (5 g), and the resulting mixture was heated on a hot water bath for 5 minutes. The mixture was cooled slightly then filtered through a pad of super-cel. The filtrate was diluted with 2-butanone (450 mL), brine (300 mL), and 1M pH 1 aqueous phosphate (150 mL). The mixture was shaken vigorously and the layers were separated. The aqueous layer was extracted with 2-butanone (2×150 mL). The combined organic layers were washed with brine (2×300 mL), dried over magnesium sulfate, filtered and evaporated to a brown solid (21.4 g). The solid was treated with ethyl acetate (100 mL), sonicated for 15 minutes and filtered. The collected solid was washed with cold ethyl acetate (50 mL) and dried under vacuum to afford 4-(2-hydroxy-ethyl)-1,8-naphthosultam as a pale brown powder (16.68 g).

$^1$H NMR (DMSO-$d_6$, 500 MHz)δ 3.25 (t, ArCH$_2$CH$_2$OH), 3.73 (m, ArCH$_2$CH$_2$OH), 4.77 (t, ArCH$_2$CH$_2$OH), 6.90 (d, H-7), 7.58 (dd, H-6), 7.69 (d, H-5), 7.69 (d, H-3), and 8.03 (d, H-2).

Step 7

4-(2-Triethylsilanyloxy-ethyl)-1 8-naphthosultam

Chlorotriethylsilane (13.57 mL, 80.86 mmol) was added dropwise over 1 minute to a vigorously stirred suspension of 4-(2-hydroxy-ethyl)-1,8-naphthosultam (17.53 g, 70.32 mmol) and imidazole (5.99 g, 87.90 mmol) in dichloromethane (351 mL). The reaction mixture was stirred under a nitrogen atmosphere at room temperature for 15 minutes, then water (350 mL) was added. The organic layer was washed sequentially with 0.2 N HCl (350 mL) and water (350 mL) then dried over magnesium sulfate, filtered, and evaporated under vacuum to a dark oil (29.07 g). The crude product was purified by flash column chromatography on silica gel (5×27 cm column, eluted with 4:1 hexanes-EtOAc followed by 3:1 hexanes-EtOAc) to afford a deep red oil (23.9 g). The oil was mixed with hexanes (225 mL), sonicated to start crystallization, and stirred at room temperature. The mixture was filtered and the collected solid was washed with hexanes (3×15 mL) and vacuum dried to afford 4-(2-triethylsilyloxy-ethyl)-1,8-naphthosultam (19.78 g) as a light pink-white solid.

$^1$H NMR (CDCl$_3$, 500 MHz)δ 0.54 (q, SiCH$_2$CH$_3$), 0.88 (t, SiCH$_2$CH$_3$), 3.34 (t, ArCH$_2$CH$_2$O), 3.95 (t, ArCH$_2$CH$_2$O), 6.89 (d, H-7), 7.14 (s, NH), 7.50 (dd, H-6), 7.62 (d, H-3), 7.66 (d, H-5), 7.89 (d, H-2)

mp 68.5–70.0° C.

PREPARATIVE EXAMPLE 2

Synthesis of 3-(2-triethylsilanyloxy-ethyl)-1,8-naphthosultam

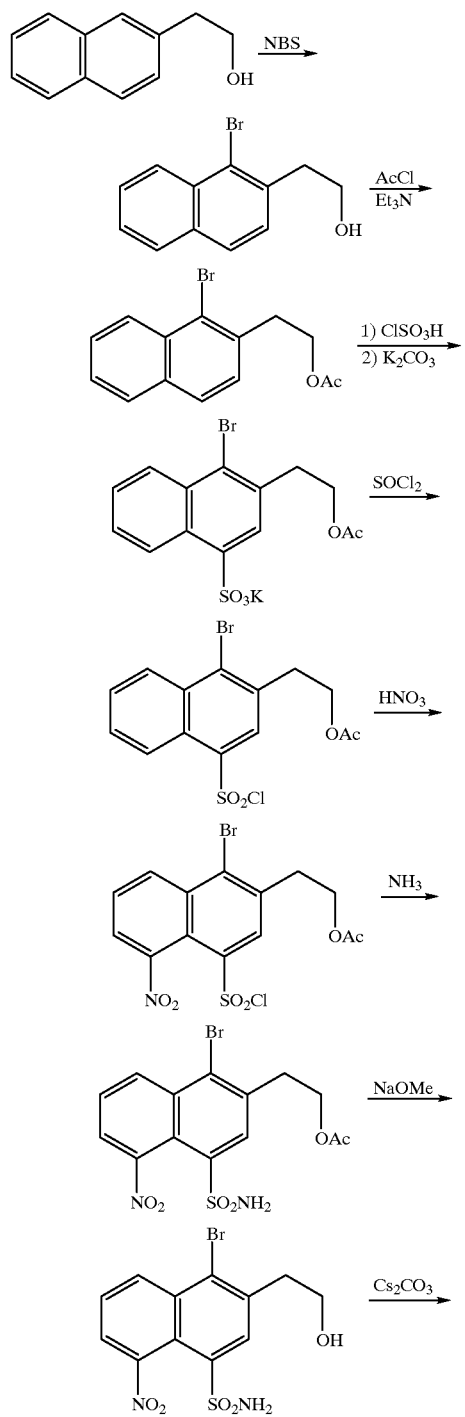

-continued

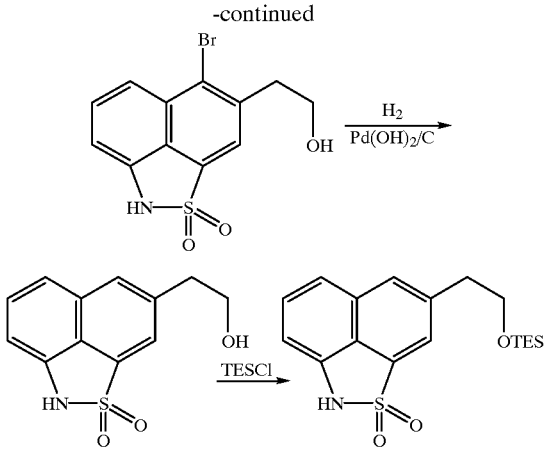

Step 1
1-Bromo-2-(2-hydroxy-ethyl)-naphthalene

A solution of 2-(2-hydroxy-ethyl)-naphthalene (58.5 g, 0.34 mol) in anhydrous acetonitrile (500 mL) was treated with N-bromo-succinimide (66.5 g, 0.37 mol). The resulting solution was stirred at room temperature under a nitrogen atmosphere and protected from light for 30 minutes, then heated in an oil bath at 50° C. for 2 hours. After cooling to room temperature, the reaction mixture was evaporated under vacuum to a viscous oil. The oil in diethyl ether (350 mL) was washed with water (350 mL), dilute aqueous sodium thiosulfate (300 mL), water (300 mL) and brine (200 mL), dried over magnesium sulfate, filtered, and evaporated under vacuum to an oil (89.5 g) that solidified on standing. The crude product was chromatographed on a column of EM silica gel 60, eluting with methylene chloride, to afford a yellow solid (78.2 g). Recrystallization of this material from carbon tetrachloride provided the title compound (46.5 g) as a pale yellow solid.

Step 2
2-(2-Acetoxy-ethyl)-1-bromo-naphthalene

A solution of 1-bromo-2-(2-hydroxy-ethyl)-naphthalene (46.5 g, 0.185 mol) in methylene chloride (370 mL) was placed under a nitrogen atmosphere, cooled in an ice bath, and stirred. Triethylamine (32.3 mL, 0.232 mol) was added followed by acetyl chloride (15.8 mL, 0.222 mol) dropwise over 5 minutes. The reaction mixture was removed from the ice bath and stirred at room temperature for 15 minutes. The reaction mixture was washed with water (300 mL), 1N hydrochloric acid (200 mL) and water (250 mL), dried over magnesium sulfate, filtered, and evaporated under vacuum to afford the title compound as an oil (55.1 g).

Step 3
Potassium 3-(2-acetoxy-ethyl)-4-bromo-naphthalene-1-sulfonate

A solution of 2-(2-acetoxy-ethyl)-1-bromo-naphthalene (32.5 g, 0.111 mol) in trifluoroacetic acid (111 mL) was stirred under a nitrogen atmosphere and cooled in an ice bath while chlorosulfonic acid (8.9 mL, 0.130 mol) was added dropwise over 5 minutes. The resulting solution was heated in an oil bath at 50° C. for 90 minutes then cooled to room temperature and evaporated under vacuum to dark oil. The oil was partitioned between methylene chloride (150 mL) and water (150 mL). The aqueous phase was washed with methylene chloride (150 mL), briefly pumped under vacuum, then brought to pH 8 with 3M aqueous potassium hydroxide (30 mL) followed by 4M aqueous potassium carbonate (35 mL). The resulting mixture was stirred in a cold room (5° C.) for 2 hours and filtered to remove the product. The recovered white solid was vacuum dried to afford the title compound (11.21 g).

Step 4
3-(2-Acetoxy-ethyl)-4-bromo-naphthalene-1-sulfonyl chloride

Potassium 3-(2-acetoxy-ethyl)-4-bromo-naphthalene-1-sulfonate (17.75 g, 43.2 mmol) was added at room temperature to a stirred solution of N,N-dimethylformamide (0.334 mL, 4.31 mmol) in thionyl chloride (63 mL, 863 mmol). The resulting mixture was placed in an oil bath at 70° C. and stirred. After 10 minutes, additional thionyl chloride (20 mL) was added to facilitate stirring. After 40 minutes at 70°, the reaction flask was fitted with a distillation head and excess thionyl chloride was removed under vacuum. The residual brown solid was mixed with diethyl ether (300 mL) and added to an ice-cold, stirred mixture of water (100 mL) and ether (100 mL). The organic phase was separated, washed with water (200 mL) and brine (100 mL), dried over magnesium sulfate, filtered, and evaporated under vacuum to afford the title compound (14.63 g).

Step 5
3-(2-Acetoxy-ethyl)-4-bromo-8-nitro-naphthalene-1-sulfonyl chloride

An ice-cold, stirred solution of 3-(2-acetoxy-ethyl)-4-bromonaphthalene-1-sulfonyl chloride (17.66 g, 45.1 mmol) in trifluoroacetic acid (150 mL) was treated with 96% sulfuric acid (12.5 mL, 225 mmol) and with 90% nitric acid (2.65 mL, 56.4 mmol) added dropwise over 3 minutes. The reaction mixture was removed from the ice bath, stirred at room temperature for 15 minutes, re-cooled in an ice bath, and treated with water (850 mL) added dropwise. The resulting mixture was filtered through a celite pad to collect the solid which was washed with water (100 mL) and dissolved in methylene chloride (350 mL). The methylene chloride solution was washed with water (500 mL) containing brine (100 mL), dried over magnesium sulfate, and evaporated under vacuum to an oil (21.23 g). This material was shown to be a 42:58 mixture of the 5-$NO_2$ to 8-$NO_2$ products by $^1$H NMR). The crude product was mixed with ethyl acetate (20 mL) and sonicated to provide a crystalline precipitate. This material was collected, washed with ethyl acetate, and dried under vacuum to afford the title compound (8.11 g, 41% yield) as an off-white solid. The mother liquors yielded an additional 1.47 g of the title compound following flash chromatography on silica gel (eluting with 30–35% ethyl acetate in hexane) and crystallization from diethyl ether.

Step 6
3-(2-Acetoxy-ethyl)-4-bromo-8-nitro-naphthalene-1-sulfonamide

Solid 3-(2-acetoxy-ethyl)-4-bromo-8-nitro-naphthalene-1-sulfonyl chloride (5.00 g, 11.45 mmol) was added at room temperature to 0.5M ammonia in dioxane (92 mL, 46 mmol). After stirring at room temperature for 40 minutes, the mixture was evaporated under vacuum to a residue which was mixed with water (100 mL), sonicated, and filtered. The collected pale-yellow solid was washed with water (2×20 mL) and vacuum dried to afford the title compound (4.75 g).

Step 7
4-Bromo-3-(2-hydroxy-ethyl)-8-nitro-naphthalene-1-sulfonamide

Sodium methoxide in methanol (23.7 mL of a 0.5M solution, 11.8 mmol) was added to a suspension of 3-(2-acetoxy-ethyl)-4-bromo-8-nitronaphthalene-1-sulfonamide (4.70 g, 11.3 mmol) in methanol (33 mL). The mixture was stirred under a nitrogen atmosphere at room temperature for 90 minutes, then concentrated under vacuum to approximately half volume, diluted with ethyl acetate (200 mL), and washed with 2N hydrochloric acid. The oganic solution was washed with water (100 mL) and brine (50 mL), dried over magnesium sulfate, filtered, and left to stand at room temperature. The organic solution deposited a solid which was collected by filtration, washed with ethyl acetate (2×15 mL), and vacuum dried to give the title comound (1.78 g). Additional poduct (1.88 g) was obtained from the mother liquors after concentration under vacuum and crystallization from diethyl ether.

Step 8
4-Bromo-3-(2-hydroxy-ethyl)-1,8-naphthosultam

A solution of 4-bromo-3-(2-hydroxy-ethyl)-8-nitro-naphthalene-1-sulfonamide (3.61 g, 9.62 mmol) in anhydrous N,N-dimethylformamide (96 mL) was treated with cesium carbonate (7.84 g, 24.1 mmol). The resulting mixture placed under a nitrogen atmospere, sonicated at room temperature for 10 minutes, stirred at room temperature for 5 minutes, and then heated in an oil bath at 100° C. for 2 hours. The mixture was evaporated under vacuum to a brown residue which was partitioned between ethyl acetate (100 mL) and 2N hydrocloric acid (20 mL). The organic phase was washed with water (20 mL) and brine (20 mL), dried over magnesium sulfate, filtered, and evaporated under vacuum to a solid (2.83 g). This material was mixed with diethyl ether (30 mL), sonicated, stirred, and filtered. The collected solid was washed with ether (20 mL) and vacuum dried to give the title compound (2.21 g) as a tan powder.

Step 9
3-(2-Hydroxy-ethyl)-1,8-naphthosultam

A solution of 4-bromo-3-(2-hydroxy-ethyl)-1,8-naphthosultam (2.10 g, 6.4 mmol) in ethanol (105 mL) was treated with triethylamine (2.68 mL, 19.2 mmol) and 20% palladium hydroxide on carbon (0.84 g). The mixture was hydrogenated (45–50 psi $H_2$) on a Parr shaker for 6.5 hours at room temperature, then filtered through a celite pad to remove the catalyst which was washed with additional ethanol (3×5 mL). The filtrate and washings were evaporated under vacuum to a residue which was partitioned between ethyl acetate (60 mL) and 1N hydrochloric acid (50 mL). The organic phase was washed with brine (25 mL), dried over magnesium sulfate, filtered, and evaporated under vacuum to afford the title compound (1.32 g) as a brown solid.

Step 10
3-(2-Triethylsilanyloxy-ethyl)-1,8-naphthosultam

A mixture of 3-(2-hydroxy-ethyl)-1,8-naphthosultam (1.44 g, 5.78 mmol) and imdazole (0.495 g, 7.27 mmol) in anhydrous methylene chloride (39 mL), at room temperature and under a nitrogen atmosphere, was treated with chlorotriethylsilane (1.12 mL, 6.69 mmol). After stirring at room temperature for 30 minutes, the mixture was diluted with methylene chloride (60 mL), washed with water (100 mL), 0.2N hydrochloric acid (50 mL) and water (100 mL), dried over magnesium sulfate, filtered, and evaporated under vacuum to a dark oil (2.15 g). The oil was purified by flash chromatography on EM silica gel 60 (4×15 cm column), using 3:1 hexane-ethyl acetate as eluting solvent, to give an oil (2.09 g). This material was mixed with hexane (10 mL) and sonicated to afford a crystalline solid. The solid was collected, washed with hexane (3 mL), and dried to afford the title compound (1.73 g).

Mp. 97.5–98.0° C.; $^1$H NMR (CDCl$_3$)δ 0.54 (q, SiCH$_2$CH$_3$), 0.88 (t, SiCH$_2$CH$_3$), 3.08 (t, ArCH$_2$), 3.90 (t, CH$_2$O), 6.84 (m, H-7), 7.24–7.47 (m, H-5 and H-6), 7.84 and 7.90 (two d's, H-2 and H-4).

PREPARATIVE EXAMPLE 3

Synthesis of N-(1-tribytylstannanyl-vinyl)-4-(2-triethylsilanyloxy-ethyl)-1,8-naphthosultam

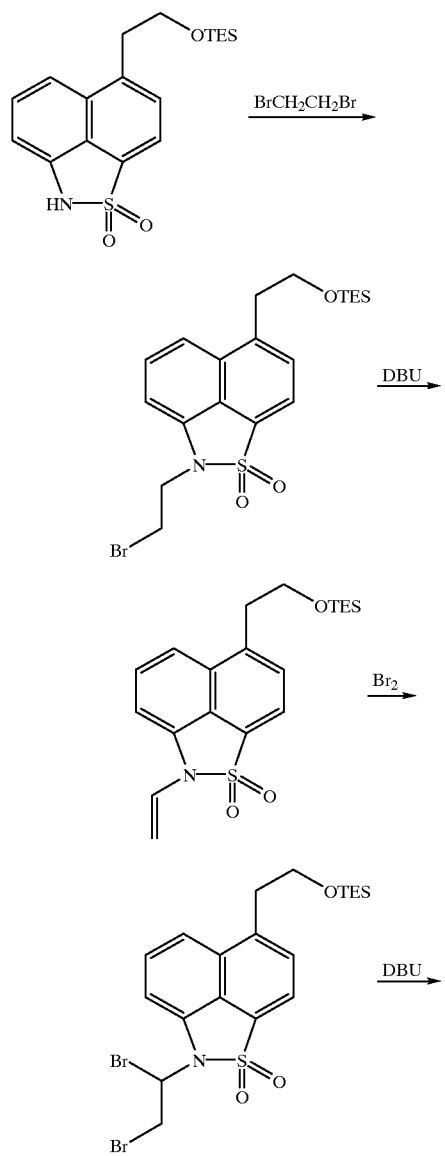

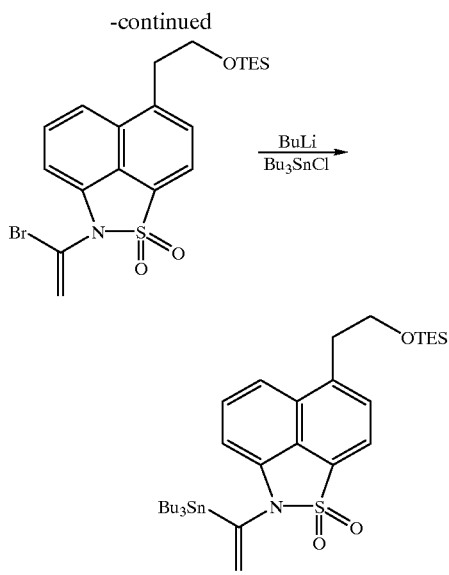

Step 1
N-(2-Bromo-ethyl)-4-(2-triethylsilanyloxy-ethyl)-1,8-naphthosultam

Potassium tert-butoxide (3.70 g, 33 mmol) is added to a solution of 4-(2-triethylsilanyloxy-ethyl)-1,8-naphthosultam (10.91 g, 30 mmol) in anhydrous dimethyl sulfoxide (30 mL). The reaction mixture is placed under a nitrogen atmosphere and stirred at room temperature for 10 minutes, then treated with 1,2-dibromo-ethane (3.1 mL, 36 mmol). The resulting mixture is stirred at room temperature for 5 minutes then heated in an oil bath at 50° C. for 21 hours. After cooling, the mixture is diluted with ethyl acetate (400 mL) and washed with water (200 mL), 0.1M hydrochloric acid (200 mL), 5% aqueous sodium bicarbonate (200 mL) and brine (200 mL). The organic phase is dried over magnesium sulfate, filtered and evaporated under vacuum. The residue is triturated with hexanes to afford the title compound.

Step 2
4-(2-Triethylsilanyloxy-ethyl)-N-vinyl-1,8-naphthosultam

A solution of crude N-(2-bromo-ethyl)-4-(2-triethylsilanyloxy-ethyl)-1,8-naphthosultam (11.29 g, 24 mmol) in anhydrous dimethyl sulfoxide (24 mL) is treated with 1,8-diazabicyclo[5.4.0]undec-7-ene (4.31 mL, 28.8 mmol). The resulting mixture is stirred under a nitrogen atmosphere and at room temperature for 24 hours. The mixture is diluted with ethyl acetate (200 mL), washed with water (4×150 mL) and brine (150 mL), dried over magnesium sulfate, filtered and evaporated under vacuum. The residue is purified by flash chromatography on silica gel to provide the title compound.

Step 3
N-(1,2-Dibromo-ethyl)-4-(2-triethylsilanyloxy-ethyl)-1,8-naphthosultam

A solution of 4-(2-triethylsilanyloxy-ethyl)-N-vinyl-1,8-naphthosultam (7.27 g, 18.66 mmol) in anhydrous dichloromethane (40 mL) is cooled in an ice-methanol bath (−20° C.) and stirred under a nitrogen atmosphere while a solution of bromine (0.97 mL, 18.83 mmol) in dichloromethane (20 mL) is added dropwise over 10 minutes. The reaction mixture is stirred an additional 15 minutes at −20° C., then evaporated under vacuum to provide the title compound.

Step 4
N-(1-Bromo-vinyl)-4-(2-triethylsilanyloxy-ethyl)-1,8-naphthosultam

A solution of crude N-(1,2-dibromo-ethyl)-4-(2-triethylsilanyloxy-ethyl)-1,8-naphthosultam (10.20 g, 18.56 mmol) in anhydrous dichloromethane (90 mL) is placed under a nitrogen atmosphere, cooled in an ice-bath, stirred, and treated dropwise with 1,8-diazabicyclo[5.4.0]undec-7-ene (2.77 mL, 18.53 mmol). After stirring at 0° C. for 90 minutes, the reaction mixture is diluted with dichloromethane (200 mL), washed with water (100 mL) and brine (100 mL), dried over magnesium sulfate, filtered, and evaporated under vacuum. The residue is purified by silica gel chromatography to afford the title compound.

Step 5
N-(1-Tributylstannanyl-vinyl)-4-(2-triethylsilanyloxy-ethyl)-1,8-naphthosultam A solution of N-(1-bromovinyl)-4-(2-triethylsilanyloxy-ethyl)-1,8-naphthosultam (0.94 g, 2 mmol) in anhydrous tetrahydrofuran (10 mL) is placed under a nitrogen atmosphere, stirred, and cooled in an acetone-dry ice bath (−78° C.). Butyllithium (1.25 mL of a 1.6M solution in hexanes, 2 mmol) is added by syringe over 5 minutes. The resulting mixture is aged at −78° C. for 10 minutes, then treated dropwise with tributyltin chloride (0.65 mL, 2.4 mmol). The mixture is allowed to gradually warm to 0° C. over 45 minutes and then diluted with ethyl acetate (100 mL), washed with water 100 mL) and brine (50 mL), dried over magnesium sulfate, filtered and evaporated under vacuum. The crude product is purified by flash chromatography on silica gel to provide the title compound.

PREPARATIVE EXAMPLE 4

Synthesis of N-(1-tributylstannyl-propyl)-4-(2-triethylsilanyoxy-ethyl)-1,8-naphthosultam

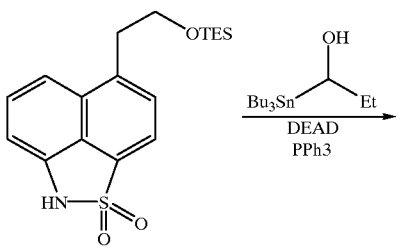

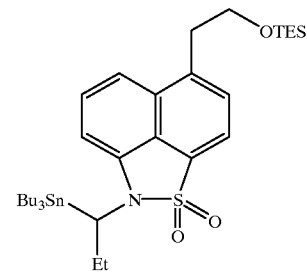

A solution of 4-(2-triethylsilanyloxy-ethyl)-1,8-naphthosultam (1.82 g, 5 mmol), 1-tributylstannyl-propan-1-ol (1.75 g, 5 mmol) and triphenylphosphine (1.57 g, 6 mmol) in anhydrous tetrahydroflran (25 mL) is placed under a nitrogen atmosphere, cooled in an ice bath, and stirred while diethyl azodicarboxylate (0.95 mL, 6 mmol) is added dropwise by syringe. The cooling bath is removed and the reaction mixture stirred at room temperature until TLC showed no further rection. The mixture is diluted with ethyl acetate (200 mL), washed with water (100 mL) and brine (100 mL), dried over magnesium sulfate, filtered, and evaporated under vacuum. The residue is purified by flash chromatography on silica gel to afford the title compound.

EXAMPLE 1

Synthesis of (1S,5R,6S)-2-(1-{4-[2-(4-carbamoylmethyl-1,4-diazonia-bicyclo[2.2.2]oct-1-yl)-ethyl]-1,8-naphthosultamyl}-vinyl)-6-[(1R)-hydroxy-ethyl]1-methyl-carbapen-2-em-3-carboxylate chloride

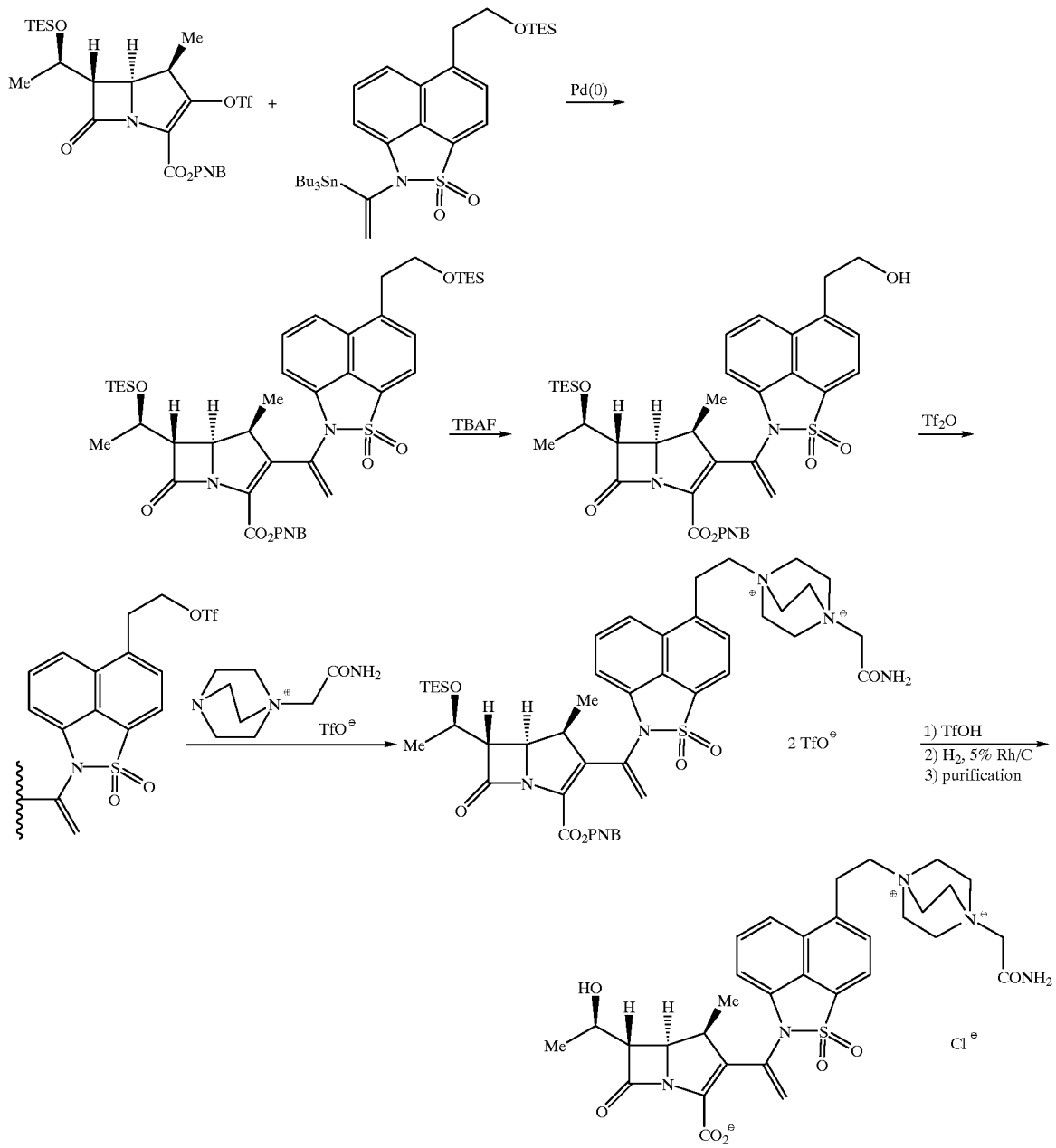

Step 1
4-Nitrobenzyl (1S,5R,6S)-1-methyl-6-[(1R)-triethylsilanyloxy-ethyl]-2-{1-[4(2-triethylsilanyloxy-ethyl)-1,8-naphthosultamyl]-vinyl}carbapen-2-em-3-carboxylate A solution of 4-nitrobenzyl (1R,5R,6S)-1-methyl-6-[(1R)-triethylsilanyloxy-ethyl]-2-(trifluoromethanesulfonyloxy)-carbapen-2-em-3-carboxylate (852 mg, 1.4 mmol) in anhydrous 1-methyl-2-pyrrolidinone (NMP, 2.8 mL) is degassed with argon then treated with zinc chloride (382 mg, 2.8 mmol), tris(2-furyl)phosphine (13 mg, 0.056 mmol), and tris(dibenzylidene-acetone)palladium(0) (26 mg, 0.028 mmol). The resulting mixture is stirred at room temperature for 10 minutes, after which time a solution of N-(1-tributylstannanyl-vinyl)-4-(2-triethylsilanyloxy-ethyl)-1,8-naphthosultam (1.140 g, 1.68 mmol) in anhydrous NMP (2.8 mL) is added dropwise over 5 minutes. The reaction mixture is stirred at room temperature and under an argon atmosphere until TLC indicated substantial consumption of the carbapenem triflate starting material. The reaction mixture is diluted with ethyl acetate (50 mL), washed with water (3×30 mL) and brine (30 mL), dried over magnesium sulfate, filtered, and evaporated under vacuum. The residue is purified by flash chromatography on EM silica gel 60 to provide the title compound.

Step 2
4-Nitrobenzyl (1S,5R,6S)-2-{1-[4-(2-hydroxy-ethyl)-1,8-naphthosultamyl]-vinyl}-1-methyl-6-[(1R)-triethylsilanyloxy-ethyl]carbapen-2-em-3-carboxylate Tetrabutylammonium fluoride (1.0 ml of a 1.0M solution in tetrahydrofuran, 1 mmol) is added to an ice-cold solution of 4-nitrobenzyl (1S,5R,6S)-1-methyl-6-[(1R)-triethylsilanyloxy-ethyl]-2-{1-[4-(2-triethylsilanyloxy-ethyl)-1,8-naphthosultamyl]-vinyl}-carbapen-2-em-3-carboxylate (848 mg, 1.0 mmol) and acetic acid (0.085 mL, 1.5 mmol) in anhydrous tetrahydrofuran (4 mL). The resulting solution is stirred at 0° C. and under a nitrogen atmosphere for 20 minutes, then partitioned between ethyl acetate (50 mL) and water (50 mL). The organic phase is washed with 5% aqueous sodium bicarbonate (25 mL) and brine (25 mL), dried over magnesium sulfate, filtered, and evaporated under vacuum. Purification of the residue by flash chromatography on silica gel affords the title compound.

Step 3
4-Nitrobenzyl (1S,5R,6S)-1-methyl-6-[(1R)-triethylsilanyloxyethyl]-2-{1-[4-(2-trifluoromethanesulfonyloxy-ethyl)-1,8-naphthosultamyl]-vinyl}-carbapen-2-em-3-carboxylate A solution of 4-nitrobenzyl (1S,5R,6S)-2-{1-[4-(2-hydroxy-ethyl)-1,8-naphthosultamyl]-vinyl}-1-methyl-6-[(1R)-triethylsilanyloxy-ethyl]carbapen-2-em-3-carboxylate (367 mg, 0.5 mmol) in anhydrous dichloromethane (10 mL) is cooled in an ice-methanol bath (−20° C.) and stirred under a nitrogen atmosphere. 2,6-Lutidine (0.175 mL, 1.5 mmol) and trifluoromethane-sulfonic anhydride (0.126 mL, 0.75 mmol) are added sequentially and the resulting solution stirred at −20° C. to −16° C. for 40 minutes. The solution is diluted with dichloromethane (30 mL), washed with water (20 mL), 0.1N hydrochloric acid (20 mL) and water (20 mL), dried over magnesium sulfate, and evaporated under vacuum to afford 4-nitrobenzyl (1S,5R,6S)-1-methyl-6-[(1R)-triethylsilanyloxyethyl]-2-{1-[4-(2-trifluoromethanesulfonyloxy-ethyl)-1,8-naphthosultamyl]-vinyl}-carbapen-2-em-3-carboxylate. The crude triflate is dissolved in anhydrous acetonitrile (4.0 mL) and this solution is used portionwise in the next step.

Step 4
4-Nitrobenzyl (1S,5R,6S)-2-(1-{4-[2-(4-carbamoylmethyl-1,4-diazonia-bicyclo[2.2.2]oct-1-yl)-ethyl]-1,8-naphthosultamyl}-vinyl)-1-methyl-6-[(1R)-triethylsilanyloxy-ethyl]-carbapen-2-em-3-carboxylate bis (trifluoro-methanesulfonate)

A solution of 4-nitrobenzyl (1S,5R,6S)-1-methyl-6-[(1R)-triethylsilanyloxy-ethyl]-2-{1-[4-(2-trifluoromethanesulfonyloxy-ethyl)-1,8-naphthosultamyl]-vinyl}-carbapen-2-em-3-carboxylate (ca. 0.125 mmol) in anhydrous acetonitrile (1.0 mL) is added to 1-(carbamoylmethyl)-1-azonia-1-aza-bicyclo[2.2.2]octane trifluoromethanesulfonate (44 mg, 0.128 mmol). The resulting solution is stirred at room temperature for 90 minutes, evaporated under vacuum and kept at room temperature for an additional 90 minutes, after which it is triturated with diethyl ether and dried under vacuum to afford the title compound.

Step 5
(1S,5R,6S)-2-(1-{4-[2-(4-carbamoylmethyl-1,4-diazonia-bicyclo[2.2.2]oct-1-yl)-ethyl]-1,8-naphthosultamyl}-vinyl)-6-[(1R)-hydroxyethyl]-1-methyl-carbapen-2-em-3-carboxylate chloride Crude 4-nitrobenzyl (1S,5R,6S)-2-(1-{4-[2-(4-carbamoylmethyl-1,4-diazonia-bicyclo[2.2.2]oct-1-yl)-ethyl]-1,8-naphthosultamyl}-vinyl)-1-methyl-6-[(1R)-triethylsilanyloxy-ethyl]-carbapen-2-em-3-carboxylate bis (trifluoro-methanesulfonate) (ca. 0.125 mmol) from the preceeding step is dissolved in 2:1 tetrahydrofuran-water (2 mL) and the solution brought to pH 2.3 by addition of 1M aqueous trifluoromethanesulfonic acid. The resulting solution is stirred at room temperature while maintaining the pH at 2.3 by additon of more trifluoromethanesulfonic acid as needed. After 75 minutes, the pH of the mixture is raised to 6.5 by addition of 1M aqueous sodium bicarbonate.

The reaction mixture is added to a mixture of butanol (1.3 mL), ethyl acetate (0.65 mL), 1M pH 7 phosphate buffer (0.65 mL), and water (1.3 mL). 5% Rhodium on carbon (15 mg) is added and the resulting mixture is sirred vigorously under a hydrogen atmosphere at room temperature. After 2 hours, the reaction mixture is filtered through a prewashed (tetrahydrofuran/water) bed of celite. The organic portion of the filtrate is separated and extracted with water (3×1 mL). The extracts are used to wash the filter cake and then combined with the original aqueous layer. The aqueous solution is washed with 1:1 ethyl acetate-diethyl ether (2×5 mL) then concentrated under vacuum to approximately 4 mL volume.

The aqueous solution is loaded onto a column of Bio-Rad Macro Prep weak cation-exchange resin (4 mL). The column is eluted with water (20 mL) followed by 5% aqueous sodium chloride (8×2 mL fractions). The product containing sodium chloride fractions (product located by UV) are cooled in an ice bath then loaded onto a column of Amberchrom CG-161 resin (5 mL). The column is eluted with ice-cold water (40 mL) followed by ambient temperature 20% aqueous isopropanol (8×2.5 mL fractions). The product containing, aqueous isopropanol fractions are diluted with an equal volume of water and concentrated under vacuum to approximately 5 mL volume. This solution is lyophilized to afford the title compound.

EXAMPLE 2

Synthesis of (1S,5R,6S)-2-(1-{4-[2-(4-carbamoylmethyl-1,4-diazonia-bicyclo[2.2.2]oct-1-yl)-ethyl]-1,8-naphthosultamyl}-propyl)-6-[1(R)-hydroxy-ethyl]-1-methyl-carbapen-2-em-3-carboxylate chloride

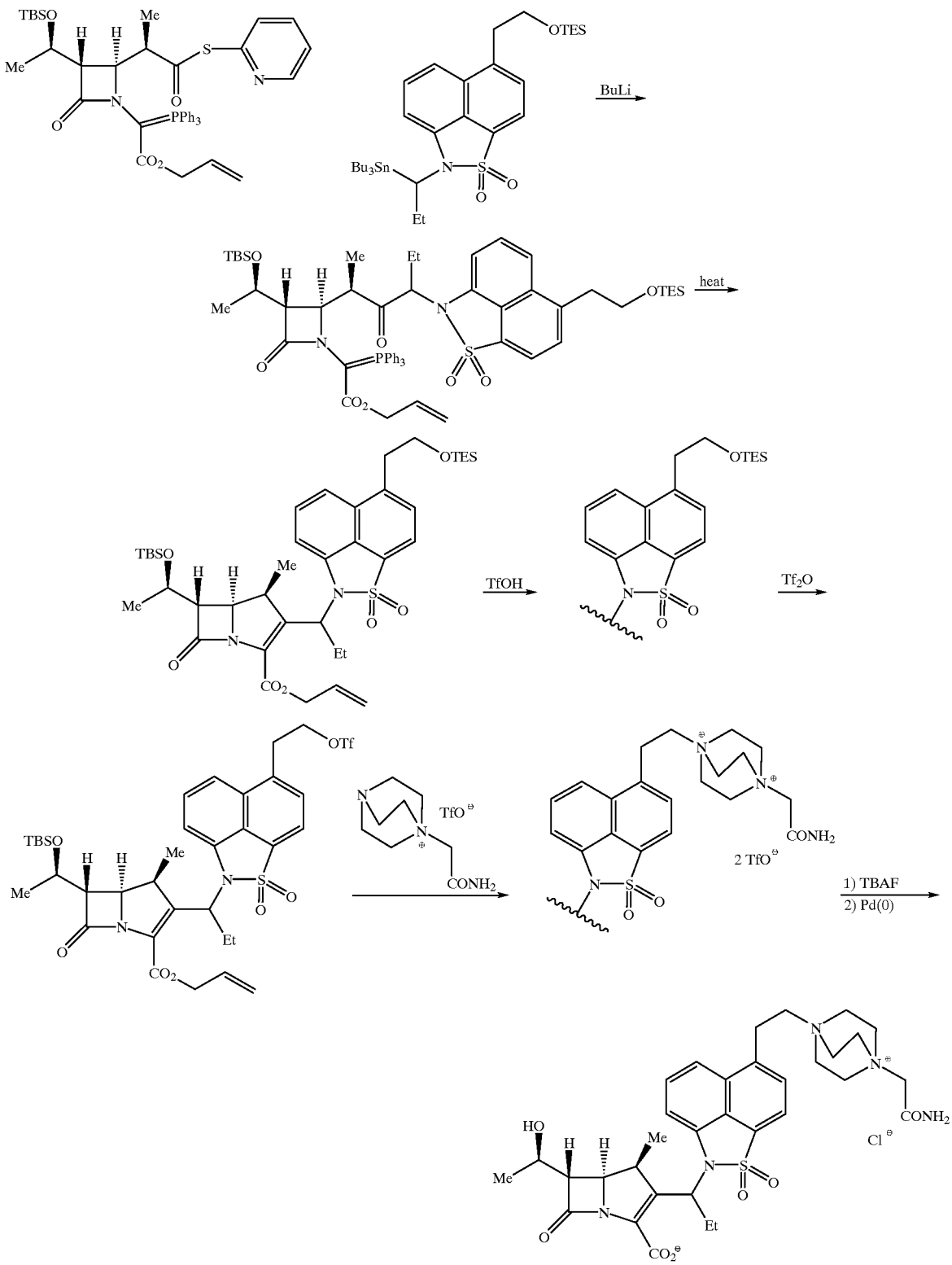

Step 1
Allyl (3-[1(R)-(tert-butyl-dimethyl-silanyloxy)-ethyl]-2-{3-[4-(2-triethylsilanyloxy-ethyl)-1,8-naphthosultamyl]-1(R)-methyl-2-oxo-pentyl}-4-oxo-(3S,4S)-azetidin-1-yl)-(triphenyl-phosphoranylidene)-acetate A solution of N-(1-tributylstannyl-propyl)-4-(2-triethylsilanyloxy-ethyl)-1,8-naphthosultam (1.39 g, 2 mmol) in anhydrous tetrahydrofuran (10 mL) is placed under a nitrogen atmosphere, cooled to −78° C., and stirred while n-butyllithium (1.25 mL of a 1.6M solution in hexanes, 2 mmol) is added dropwise. After an additional 10 minutes at −78° C., the solution is transferred via Teflon tubing to a precooled (−78° C.) solution of allyl {3-[1(R)-(tert-butyl-dimethyl-silanyloxy)-ethyl]-2-oxo-4-[1(R)-(pyridin-2-ylthiocarbonyl)-ethyl]-(3S,4S)-azetidin-1-yl}-(triphenyl-phosphoranylidine)-acetate (1.51 g, 2 mmol) in anhydrous tetrahydrofuran (10 mL). The resulting solution is stirred under a nitrogen atmosphere at −78° C. for 30 minutes, then allowed to gradually warm to 0° C. over a period of 60 minutes. The reaction mixture is diluted with water (50 mL) and extracted with ethyl acetate (3×50 mL). The combined organic extracts are washed with water (100 mL) and brine (100 mL), dried over magnesium sulfate, filtered, and concentrated under vacuum. The crude product is purified by chronatography on silica gel to afford the title compound.

Step 2

Allyl (1S,5R,6S)-6-[1(R)-(tert-butyl-dimethyl-silanyloxy)-ethyl]-1-methyl-2-{1-[4-(2-triethylsilanyloxy-ethyl)-1,8-naphthosultamyl]-propyl}-carbapen-2-em-3-carboxylate A solution of allyl (3-[1(R)-(tert-butyl-dimethyl-silanyloxy)-ethyl]-2-{3-[4-(2-triethylsilanyloxy-ethyl)-1,8-naphthosultamyl]-1(R)-methyl-2-oxo-pentyl}-4-oxo-(3S, 4S)-azetidin-1-yl)-(triphenyl-phosphoranylidene)-acetate (1.26 g, 1.2 mmol) in toluene (80 mL) is placed under a nitrogen atmosphere and heated at reflux until TLC showed complete conversion of the ylide to products. The solvent is removed in vacuum and the residue purified by silica gel chromatography to give the title compound as a mixture of diastereomers. The diastereomeric mixture is processed as described in steps 3–5.

Alternatively, the diastereomeric mixture is separated by silica gel column chromatograpy or by preparative HPLC. The individual diastereomers, isomeric at the 2'-position, are processed according to steps 3–5 to give diastereomerically pure final products.

Step 3

Allyl (1S,5R,6S)-6-[1(R)-(tert-butyl-dimethyl-silanyloxy)-ethyl]-1-methyl-2-(1-{4-[2-(trifluoro-methanesulfonyloxy)-ethyl]-1,8-naphthosultamyl}-propyl)-carbapen-2-em-3-carboxylate A solution of allyl (1S,5R,6S)-6-[1(R)-(tert-butyl-dimethyl-silanyloxy)-ethyl]-1-methyl-2-{1-[4-(2-triethylsilanyloxy-ethyl)-1,8-naphthosultamyl]-propyl}-carbapen-2-em-3-carboxylate (300 mg, 0.39 mmol) in tetrahydrofuran (3.1 mL) is diluted with water (0.8 mL), treated with 1M aqueous trifluoromethanesulfonic acid (0.039 mL, 0.039 mmol), and stirred at room temperature for 15 minutes. The mixture is partitioned between ethyl acetate (30 mL) and 5% aqueous sodium bicarbonate (10 mL). The organic layer is washed with 50% brine (10 mL), dried over magnesium sulfate, filtered, evaporated under vacuum, and stripped with toluene to provide crude allyl (1S,5R,6S)-6-[1(R)-(tert-butyl-dimethyl-silanyloxy)-ethyl]-2-{1-[4-(2-hydroxy-ethyl)-1,8-naphthosultamyl]-propyl}-1-methyl-carbapen-2-em-3-carboxylate.

The crude alcohol (ca. 0.39 mmol) is dissolved in anhydrous dichloromethane (7.8 mL) and the solution is cooled in an ice-methanol bath (−20° C.) and stirred under a nitrogen atmosphere. 2,6-Lutidine (0.135 mL, 1.16 mmol) and trifluoro-methanesulfonic anhydride (0.098 mL, 0.58 mmol) are added sequentially. The reaction mixture is stirred at −20° C. to −15° C. for 40 minutes, then diluted with dichloromethane (25 mL) and washed with water (20 mL), 0.1N hydrochloric acid (20 mL) and 50% brine (20 mL). The organic layer is dried over magnesium sulfate, filtered, and evaporated under vacuum to provide the title compound.

Step 4

Allyl (1S,5R,6S)-6-[1(R)-(tert-butyl-dimethyl-silanyloxy)-ethyl]-2-(1-{4-[2-(4-carbamoylmethyl-1,4-diazonia-bicyclo[2.2.2]oct-1-yl)-ethyl]-1,8-naphthosultamyl}-propyl)-1-methyl-carbapen-2-em-3-carboxylate bis(trifluoro-methanesulfonate)

A solution of allyl (1S,5R,6S)-6-[1(R)-(tert-butyl-dimethyl-silanyloxy)-ethyl]-1-methyl-2-(1-{4-[2-(trifluoro-methanesulfonyloxy)-ethyl]-1,8-naphthosultamyl}-propyl)-carbapen-2-em-3-carboxylate (98 mg, 0.125 mmol) in anhydrous acetonitrile (1.0 mL) is added to 1-(carbamoylmethyl)-1-azonia-1-aza-bicyclo[2.2.2]octane trifluoro-methanesulfonate (44 mg, 0.128 mmol). The resulting solution is stirred at room temperature for 90 minutes, evaporated under vacuum, and kept at room temperature for an additional 90 minutes. The product is triturated with diethyl ether and the insoluble portion dried under vacuum to afford the title compound.

Step 5

(1S,5R,6S)-2-(1-{4-[2-(4-carbamoylmethyl-1,4-diazonia-bicyclo[2.2.2]oct-1-yl)-ethyl]-1,8-naphthosultamyl}-propyl)-[6-1(R)-hydroxy-ethyl]-1-methyl-carbapen-2-em-3-carboxylate chloride A solution of crude allyl (1S,5R,6S)-6-[1(R)-(tert-butyl-dimethyl-silanyloxy)-ethyl]-2-(1-{4-[2-(4-carbamoylmethyl-1,4-diazonia-bicyclo[2.2.2]oct-1-yl)-ethyl]-1,8-naphthosultamyl}-propyl)-1-methyl-carbapen-2-em-3-carboxylate bis(trifluoro-methanesulfonate) (ca. 0.125 mmol) in anhydrous acetonitrile (1.0 mL) is diluted with anhydrous tetrahydrofuran (1.5 mL) and then treated with acetic acid (0.11 mL, 1.92 mmol) and tetrabutylammonium fluoride (0.63 mL of a 1M tetrahydrofuran solution, 0.63 mmol). The resulting mixture is stirred at room temperature and under a nitrogen atmosphere for 25 hours. The solvents are removed under vacuum and the residue is triturated with several portions of diethyl ether. The material is dried under vacuum to afford crude allyl (1S,5R,6S)-2-(1-{4-[2-(4-carbamoylmethyl-1,4-diazonia-bicyclo[2.2.2]oct-1-yl)-ethyl]-1,8-naphthosultamyl}-propyl)-6-[1(R)-hydroxy-ethyl]-1-methyl-carbapen-2-em-3-carboxylate bis(trifluoro-methanesulfonate).

The above product (ca. 0.125 mmol), triphenylphosphine (4.9 mg, 0.0187 mmol), dimedone (53 mg, 0.378 mmol), and tetrakis(triphenylphospine)palladium(0) (7.2 mg, 0.0062 mmol) are dissolved in anhydrous N,N-dimethylformamide (1.3 mL). The solution is purged with nitrogen, then treated with N,N-diisopropylethylamine (0.065 mL, 0.373 mmol) and stirred at room temperature for 15 minutes. The reaction mixture is added to diethyl ether (10 mL) to precipitate the crude product. This material is triturated with ether (2×5 mL) and the insoluble portion dried under vacuum.

The crude product is dissolved in 1:1 acetonitrile-water (1 mL) and the solution loaded onto a column of Bio-Rad Macro Prep CM ion exchange resin (3 mL). The column is eluted with 1:1 acetonitrile-water (4 mL), water (3×5 mL), and 5% aqueous sodium chloride (10×2 mL). The product containing NaCl fractions are cooled in ice then loaded onto a column of Amberchrom CG-161 resin (3 mL). The column is eluted with ice-cold water (3×5 mL) followed by ambient temperature 20% aqueous isopropanol (5×3 mL). The product containing 20% iPrOH fractions are combined, diluted with water (5 mL), concentrated under vacuum to ca. 4 mL volume, and lyophilized to afford the title compound.

EXAMPLES 3–56

By appropriately modifying the procedures of Preparative Examples 3 and 4 and of Examples 1 and 2, the following compounds are prepared:
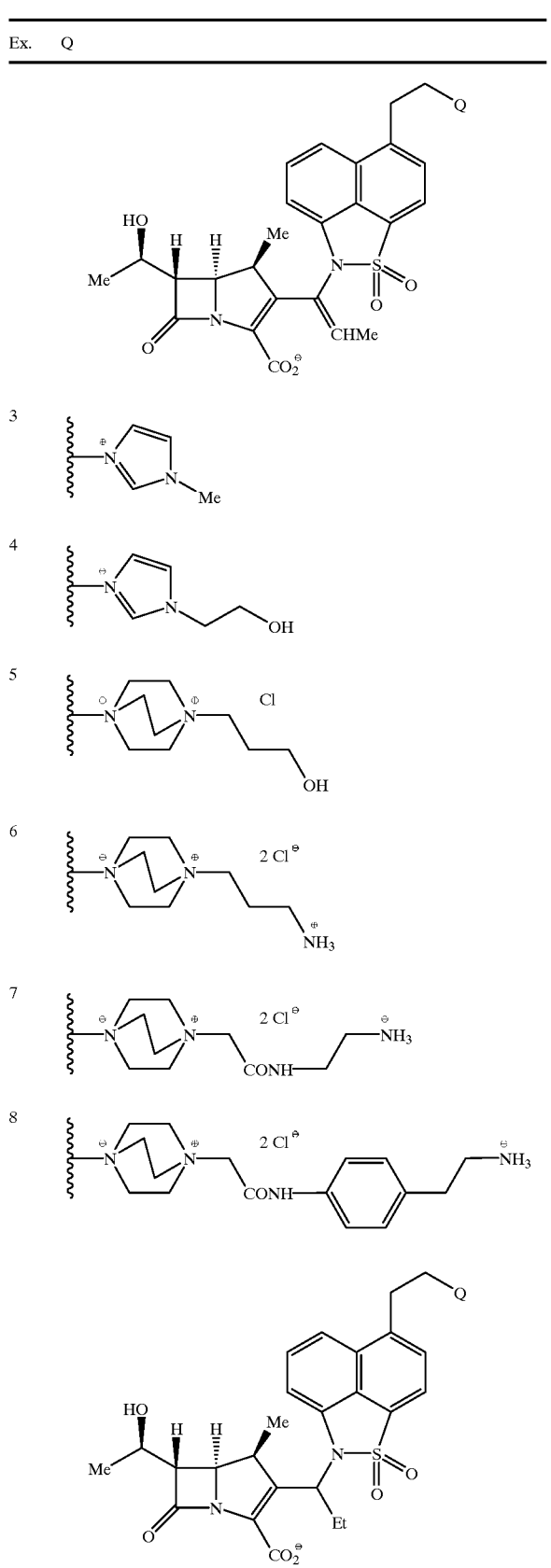
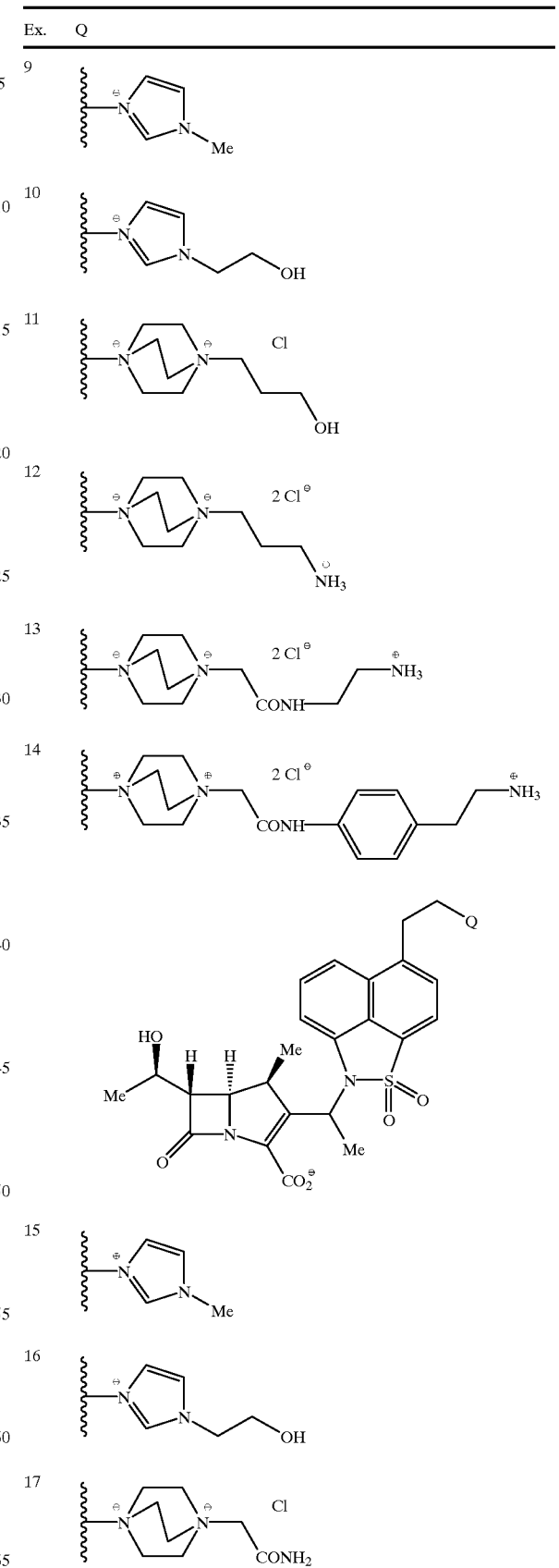

-continued
| Ex. | Q |
|---|---|
| 18 | 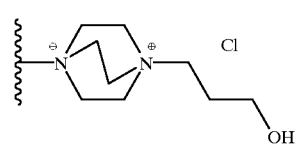 |
| 19 | 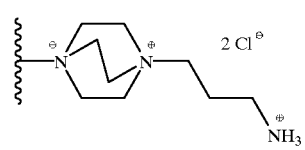 |
| 20 | 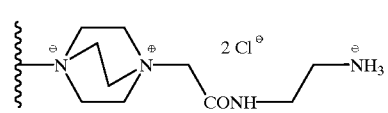 |
| 21 | 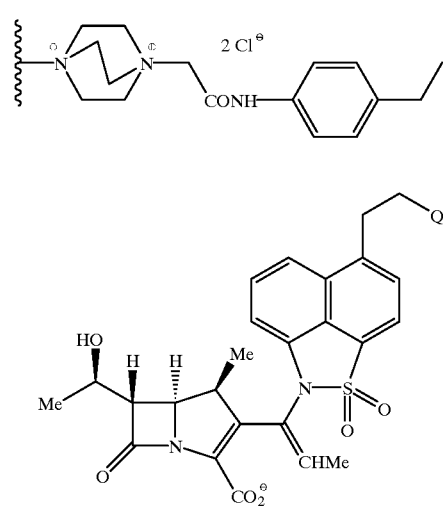 |
| 22 | 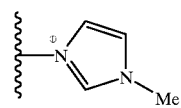 |
| 23 | 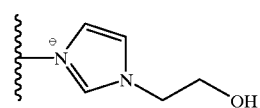 |
| 24 | 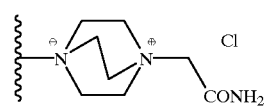 |
| 25 | 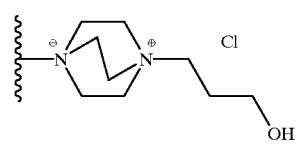 |
-continued
| Ex. | Q |
|---|---|
| 26 | 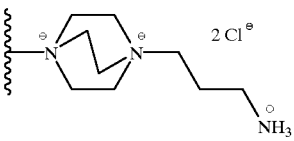 |
| 27 | 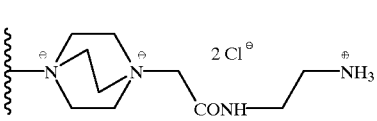 |
| 28 | 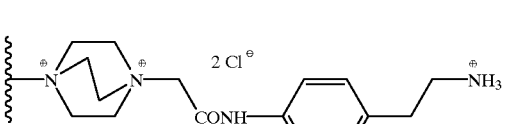 |
| | 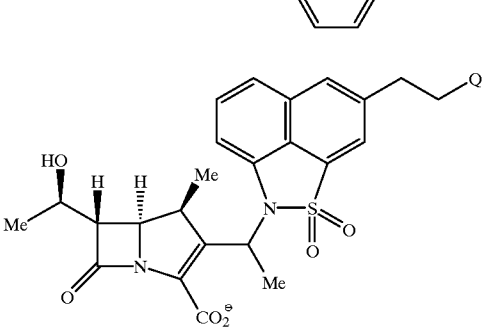 |
| 29 | 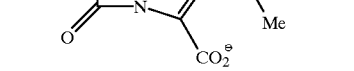 |
| 30 | 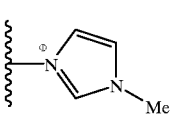 |
| 31 | 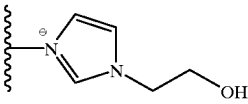 |
| 32 | 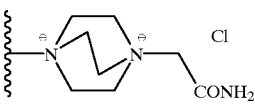 |
| 33 | 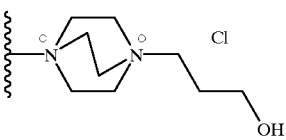 |
| 34 | 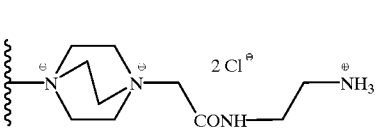 |

-continued
| Ex. | Q |
|---|---|
| 35 | 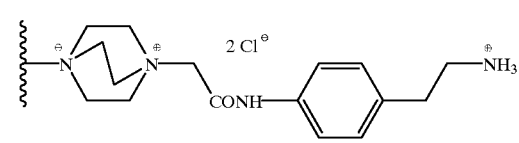 |
| | 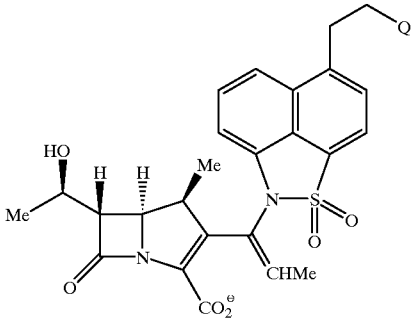 |
| 36 | 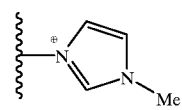 |
| 37 | 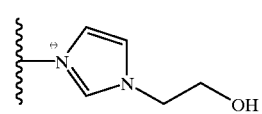 |
| 38 | 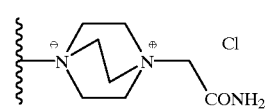 |
| 39 | 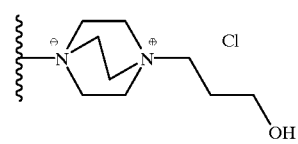 |
| 40 | 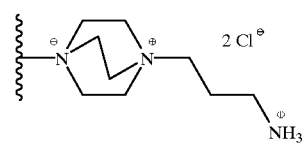 |
| 41 | 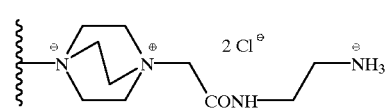 |
| 42 | 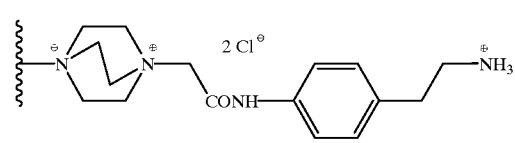 |
-continued
| Ex. | Q |
|---|---|
| | 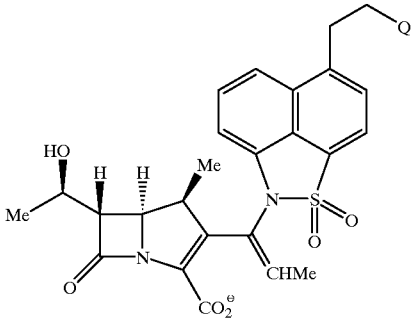 |
| 43 | 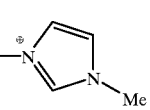 |
| 44 | 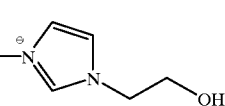 |
| 45 | 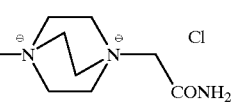 |
| 46 | 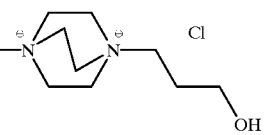 |
| 47 | 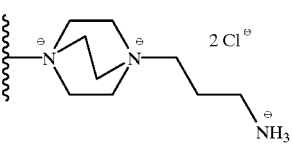 |
| 48 | 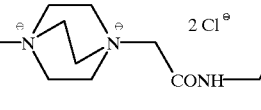 |
| 49 | 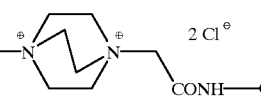 |
| | 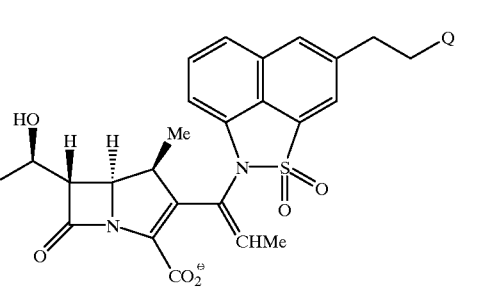 |

-continued

| Ex. | Q |
|---|---|
| 50 | 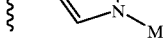 |
| 51 | 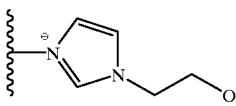 |
| 52 | 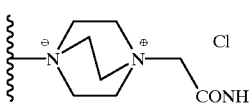 |
| 53 | 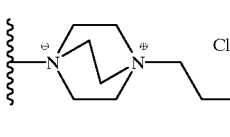 |
| 54 | 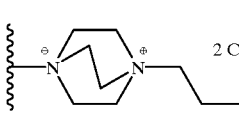 |
| 55 | 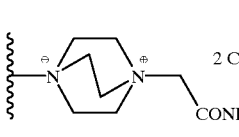 |
| 56 | 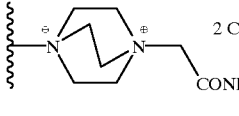 |

What is claimed is:

1. A compound represented by formula I:

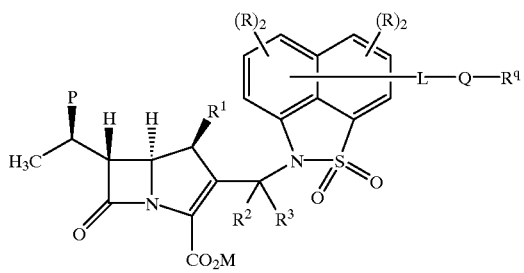

including pharmaceutically acceptable salts thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

$R^2$ and $R^3$ taken in combination represent $C_{1-3}$ alkylidene;

L is $C_{1-4}$ straight or branched alkylene, uninterrupted, interrupted or terminated by O, S, $NR^a$, C(O), $CO_2$ and $C(O)NR^a$;

Q represents:

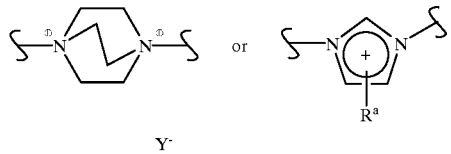

$Y^-$ is a charge balancing group;

$R^a$ is H or C1–6 alkyl;

$R^q$ is $C_{1-6}$ alkyl, straight or branched, uninterrupted, interrupted or terminated by 1–2 of O, S, $NR^a$, C(O), C(O)O, $C(O)NR^a$, —CH=CH—, $-Het(R^b)_3$—, $—C(O)Het(R^b)_3$—, $—C(O)NR^aHet(R^b)_3$—

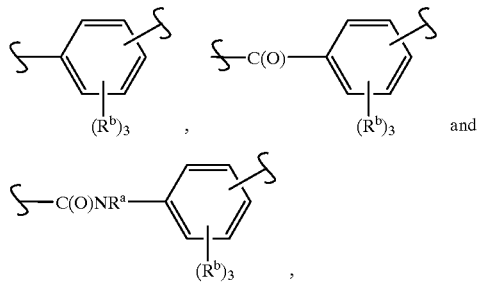 and

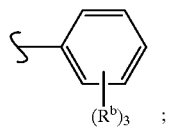 , said $R^q$ being unsubstituted or substituted with 1–3 $R^c$ groups;

Het is a heteroaryl group;

each $R^b$ is independently selected from H, halo, $OR^a$, $OC(O)R^a$, $C(O)R^a$, CN, $C(O)NR^aR^d$, $NO_2$, $NR^aR^d$, $SO_2NR^aR^d$ and $C_{1-4}$ alkyl unsubstituted or substituted with 1–3 groups selected from $R^e$;

each $R^c$ is independently selected from halo, $C_{1-4}$ alkyl, $OR^f$, $OC(O)R^f$, $SR^f$, $S(O)R^f$, $SO_2R^f$, CN, $C(O)R^f$, $CO_2R^f$, $NR^fR^g$, $C(O)NR^aR^f$, $-Het(R^b)_3$, $C(=N^+R^aR^f)R^a$, heteroarylium$(R^b)_3$, $SO_2NR^aR^f$, $OC(O)NR^aR^f$, $NR^aC(O)R^f$, $NR^aC(O)NR^aR^f$, and

 ;

or in the alternative, when 2 or more $R^c$ groups are present, 2 $R^c$ groups may be taken together with any intervening atoms to form a 3–6 membered carbocyclic ring, optionally interrupted with 1–3 of O, S, $NR^g$, and C(O), said ring being unsubstituted or substituted with 1–3 $R^e$ groups, $R^d$ is H or $C_{1-4}$ alkyl;

each $R^e$ is independently selected from halo, $OR^a$, $NR^aR^d$ and $CONR^aR^d$;

$R^f$ is H; $C_{1-6}$ straight or branched chain alkyl, unsubstituted or substituted with 1–3 $R^e$ groups; $-Het(R^b)_3$; $C_{3-6}$ cycloalkyl, unsubstituted or substituted with 1–3 $R^e$ groups, and

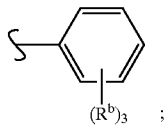

$R^g$ is H, $C_{1-6}$ alkyl, unsubstituted or substituted with 1–3 $R^e$ groups; $C_{3-6}$ cycloalkyl, unsubstituted or substituted with 1–3 $R^e$ groups; $C(=N^+R^aR^f)R^a$ or $C(=N^+R^aR^f)NR^aR^f$;

and each R independently represents $R^b$,

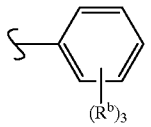

-Het$(R^b)_3$ or C2–6 alkenyl, where necessary, said compounds are balanced with one or more of a charged balancing group $X^-$.

2. A compound in accordance with claim 1 wherein $R^1$ represents methyl.

3. A compound in accordance with claim 1 wherein $CO_2M$ represents a carboxylate anion.

4. A compound in accordance with claim 1 wherein P represents hydroxyl or hydroxyl protected by a hydroxyl protecting group.

5. A compound in accordance with claim 1 wherein $R^2$ and $R^3$ are taken in combination, and represent $C_{1-3}$ alkylidene.

6. A compound in accordance with claim 1 wherein $R^2$ and $R^3$ are taken in combination to represent $=CH_2$ or $=CHMe$.

7. A compound in accordance with claim 1 wherein L represents $—CH_2—$ or $—CH_2CH_2—$.

8. A compound in accordance with claim 1 wherein Q represents

in which $Y^-$ represents a charge balancing group.

9. A compound in accordance with claim 1 wherein $R^q$ is straight or branched $C_{1-6}$ alkyl, optionally interrupted by $—C(O)NR^a—$ or

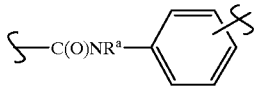

and substituted with 1–3 $R^e$ groups.

10. A compound represented by formula I

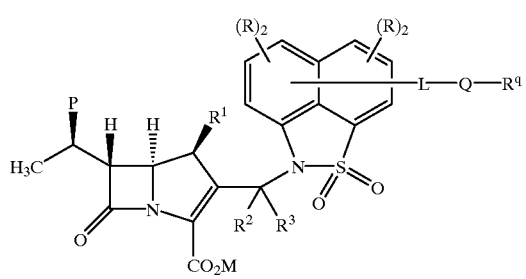

or a pharmaceutically acceptable salt thereof, wherein:

$R^1$ represents methyl;

$CO_2M$ represents a carboxylate anion;

P represents hydroxyl or hydroxyl protected by a hydroxyl protecting group;

each R is independently H, halo or $C_{1-4}$ alkyl unsubstituted or substituted with 1–3 groups selected from $R^e$;

$R^a$ is H or C1–6 alkyl;

$R^d$ is H or $C_{1-4}$ alkyl;

$R^e$ is halo, $OR^a$, $NR^aR^d$ or $CONR^aR^d$;

$R^2$ and $R^3$ are taken in combination, and represent $C_{1-3}$ alkylidene;

L represents $—CH_2—$ or $—CH_2CH_2—$;

Q represents

wherein $Y^-$ represents a charge balancing group and $R^q$ is straight or branched $C_{1-6}$ alkyl, optionally interrupted by $C(O)NR^a$ or

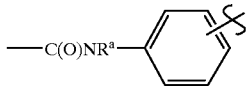

and substituted with 1–3 $R^e$ groups.

11. A compound in accordance with claim 10 wherein $R^2$ and $R^3$ are taken in combination to represent $=CH_2$ or $=CHMe$.

12. A compound having a structure in accordance with the following:

TABLE I
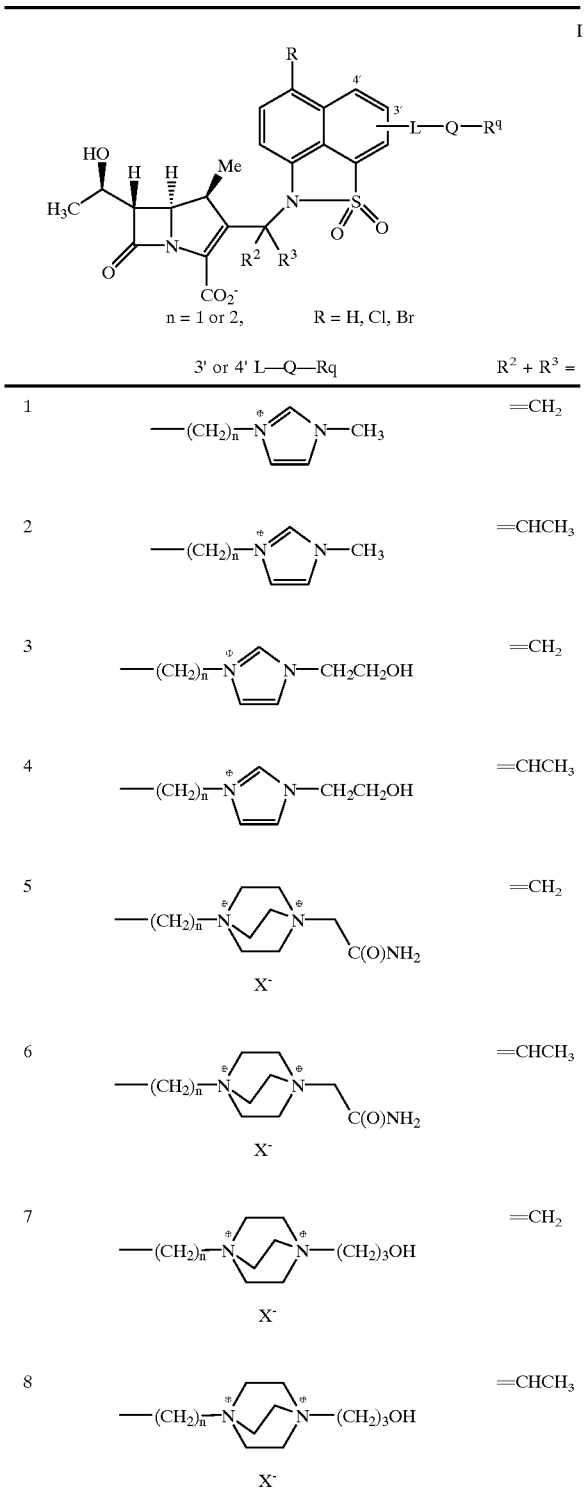
TABLE I-continued
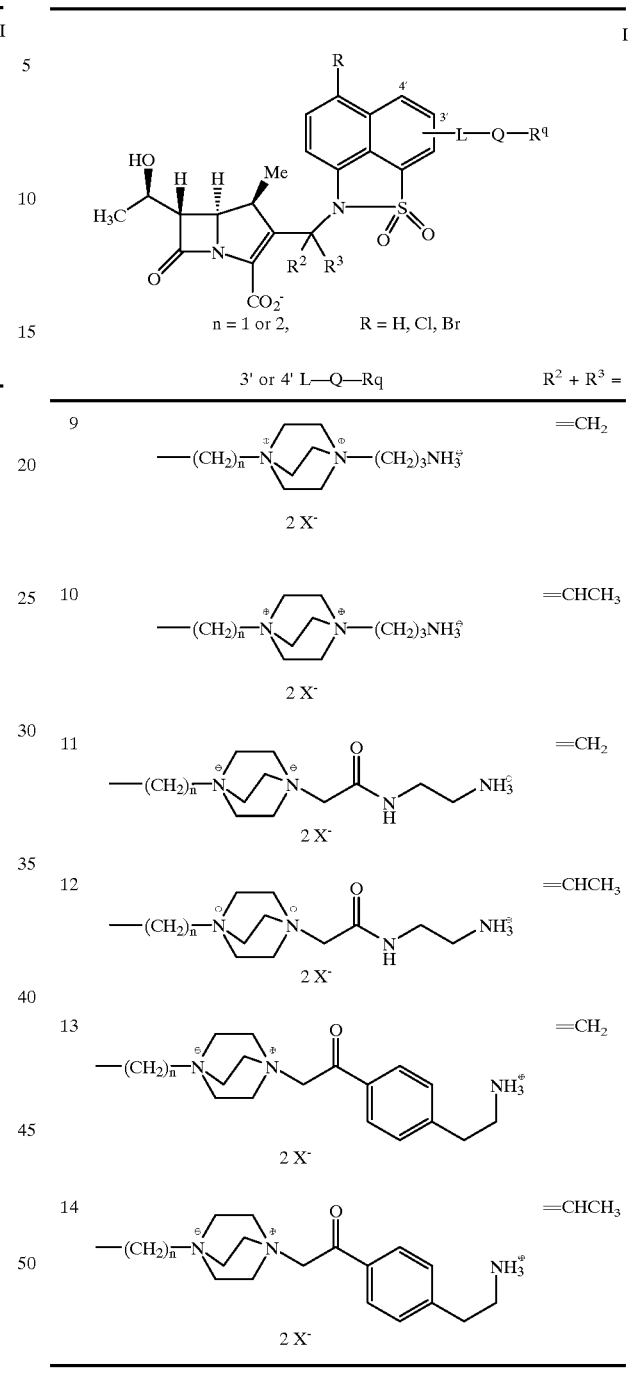
wherein X⁻ represents a counterion.
13. A compound having a structural formula in accordance with one of the following:

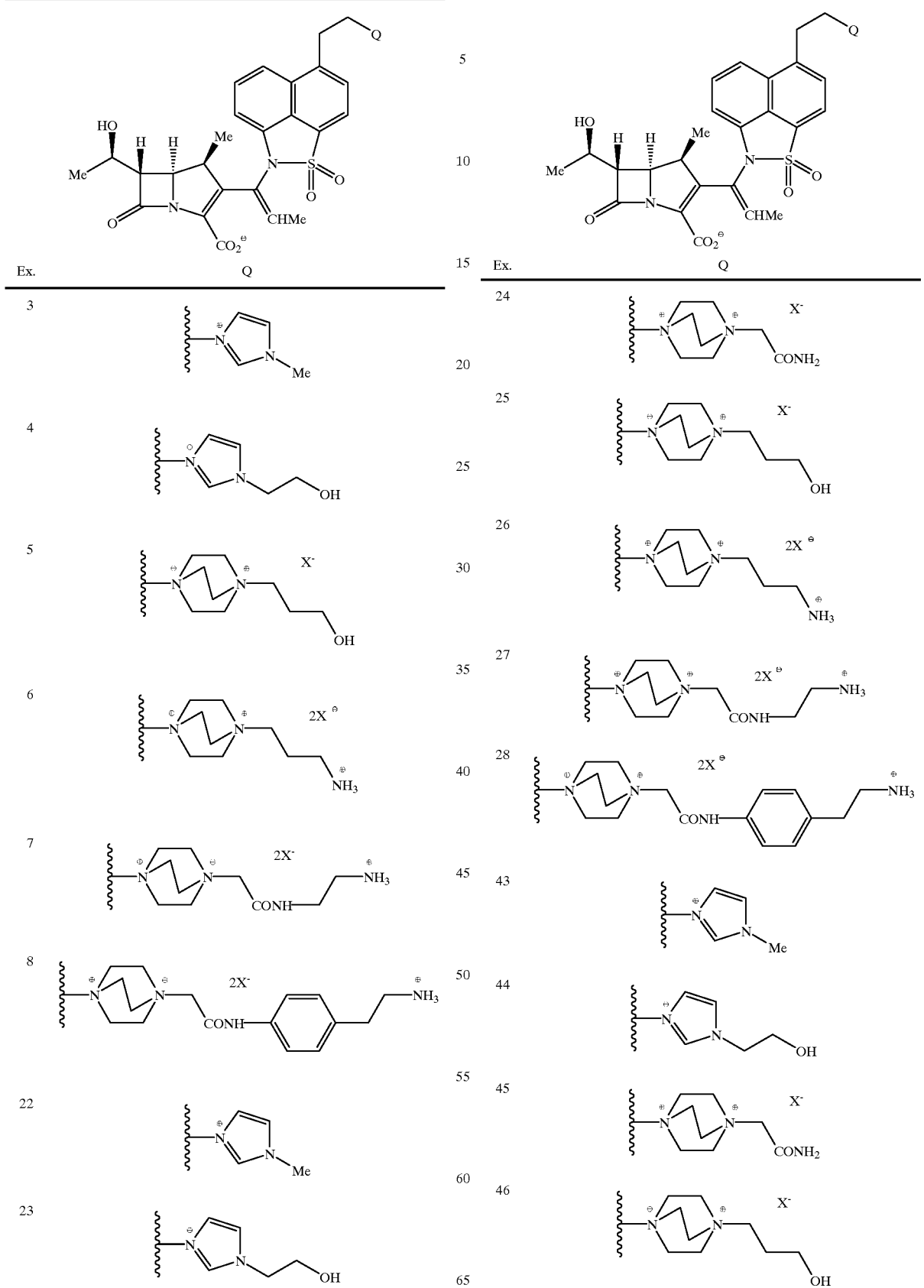

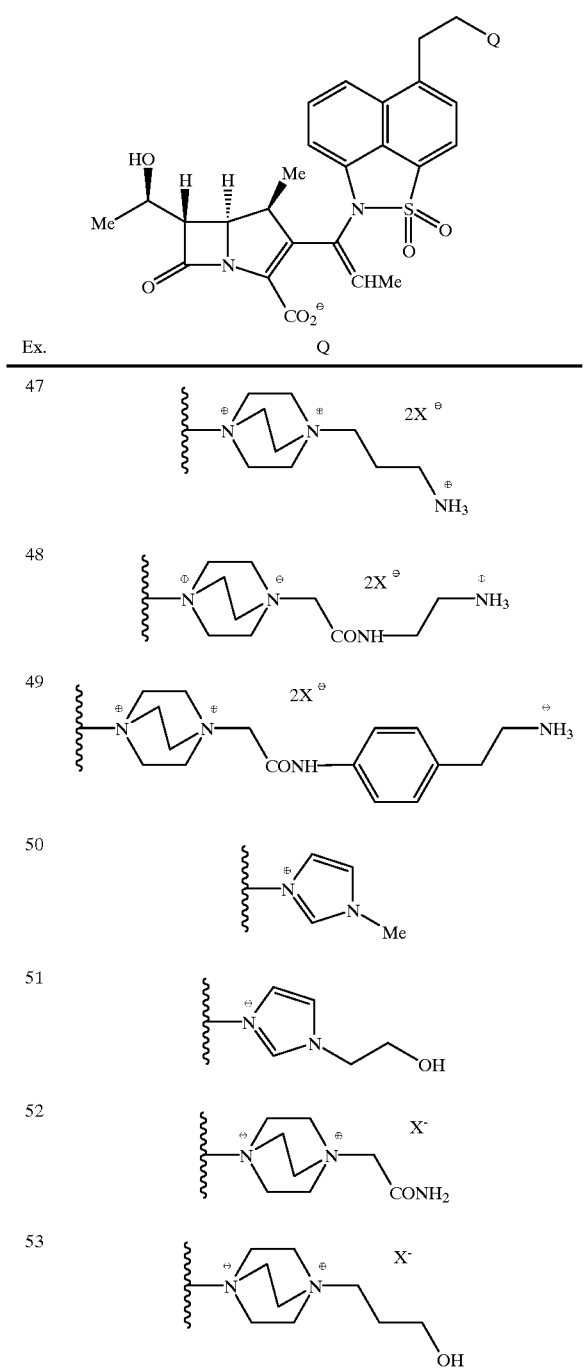

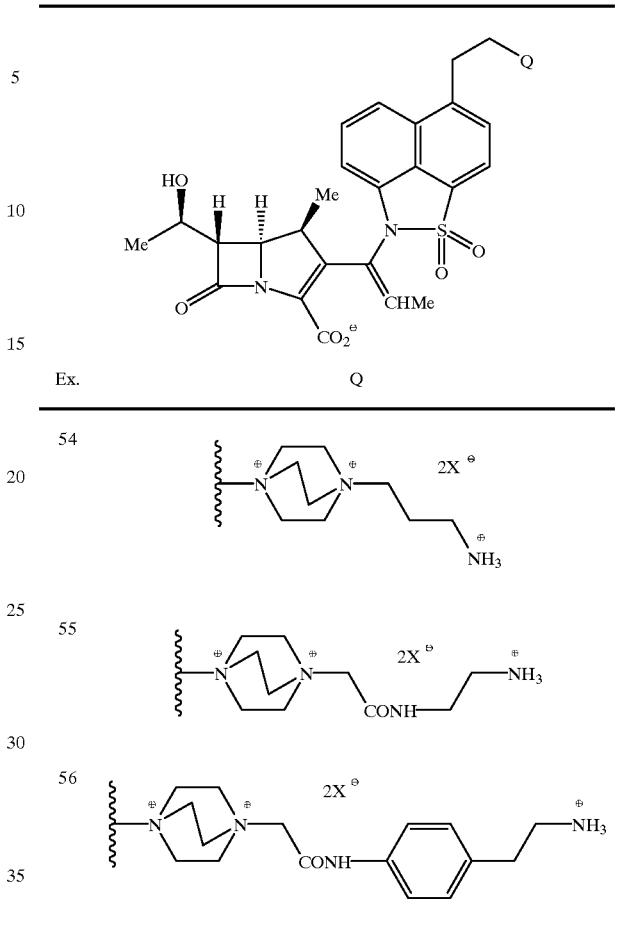

wherein X⁻ is a counterion.

14. A pharmaceutical composition comprised of a compound in accordance with claim 1 in combination with a pharmaceutically acceptable carrier.

15. A method of treating a bacterial infection comprising administering to a mammalian patient in need of such treatment a compound as defined in claim 1 in an amount which is effective for treating a bacterial infection.

* * * * *